US012409469B2

(12) United States Patent
Wilcox et al.

(10) Patent No.: US 12,409,469 B2
(45) Date of Patent: Sep. 9, 2025

(54) APPARATUS FOR GENERATING DRY MIST

(71) Applicants: Bryan K. Wilcox, Cecar City, UT (US); Kenton T. Meadows, Cedar City, UT (US)

(72) Inventors: Bryan K. Wilcox, Cecar City, UT (US); Kenton T. Meadows, Cedar City, UT (US)

( * ) Notice: Subject to any disclaimer, the term of this patent is extended or adjusted under 35 U.S.C. 154(b) by 474 days.

(21) Appl. No.: 17/932,581

(22) Filed: Sep. 15, 2022

(65) Prior Publication Data
US 2023/0083760 A1 Mar. 16, 2023

Related U.S. Application Data

(60) Provisional application No. 63/244,544, filed on Sep. 15, 2021.

(51) Int. Cl.
B05B 17/06 (2006.01)
A61L 2/22 (2006.01)
A61L 2/26 (2006.01)
A61L 9/14 (2006.01)
A61L 101/06 (2006.01)
B05B 7/00 (2006.01)

(52) U.S. Cl.
CPC ............ B05B 17/0615 (2013.01); A61L 2/22 (2013.01); A61L 2/26 (2013.01); A61L 9/14 (2013.01); A61L 2101/06 (2020.08); A61L 2202/14 (2013.01); A61L 2202/15 (2013.01); A61L 2202/16 (2013.01); A61L 2209/111 (2013.01); A61L 2209/132 (2013.01); B05B 7/0012 (2013.01); B05B 7/0093 (2013.01)

(58) Field of Classification Search
CPC ... A61L 2/22; A61L 2/26; A61L 19/14; A61L 2101/06; A61L 2202/14; A61L 2202/15; A61L 2202/16; A61L 2209/111; A61L 2209/132; B05B 7/0012; B05B 7/0093; B05B 17/0615
USPC .................................................. 239/4, 102.2
See application file for complete search history.

(56) References Cited

U.S. PATENT DOCUMENTS 3,472,455 A * 10/1969 Johnson ................ A61M 15/00
261/78.2
4,612,777 A *  9/1986 Noma ................... A47F 3/0447
261/118
4,641,680 A *  2/1987 Been ...................... B65D 90/24
4/321
5,361,989 A * 11/1994 Merchat ............. B05B 17/0615
239/524

(Continued)

FOREIGN PATENT DOCUMENTS

CN    106152356 A    11/2016
CN    109092616 A  * 12/2018 ............ B05B 17/06

(Continued)

Primary Examiner — Joseph A Greenlund
Assistant Examiner — Kevin Edward Schwartz
(74) Attorney, Agent, or Firm — Gurr & Brande, PLLC; Robert A. Gurr

(57) ABSTRACT

A dry mist generating apparatus has a plastic housing, an ultrasonic transducer, a fan inducing airflow within the plastic housing, a diffuser plate for directing airflow, increasing velocity, and decreasing pressure, at least one opening for releasing the resulting dry mist, and a reservoir for capturing droplets that exceed 4 microns.

1 Claim, 25 Drawing Sheets

(56) References Cited

U.S. PATENT DOCUMENTS

| | | | |
|---|---|---|---|
| 5,693,266 A * | 12/1997 | Jung | B01F 23/2133 |
| | | | 261/80 |
| 8,001,962 B2 * | 8/2011 | Sheiman | B05B 17/063 |
| | | | 239/338 |
| 10,639,666 B2 * | 5/2020 | Kim | B05B 1/02 |
| 2006/0213508 A1 | 9/2006 | Murray et al. | |
| 2006/0214026 A1 | 9/2006 | Nomura et al. | |
| 2008/0245362 A1 | 10/2008 | Moessis et al. | |
| 2011/0226868 A1 * | 9/2011 | Modlin | B05B 17/0684 |
| | | | 239/102.1 |
| 2016/0010881 A1 * | 1/2016 | Moon | B01D 53/145 |
| | | | 96/245 |
| 2017/0203323 A1 | 7/2017 | Gschwind et al. | |
| 2021/0393833 A1 * | 12/2021 | Cunningham | B05B 7/08 |
| 2022/0313848 A1 * | 10/2022 | Oh | B05B 7/0012 |

FOREIGN PATENT DOCUMENTS

| | | | | |
|---|---|---|---|---|
| JP | H08309248 A | * | 11/1996 | B05B 17/06 |
| JP | 2004216221 A | * | 8/2004 | B05B 17/0615 |
| JP | 2012143684 A | * | 8/2012 | B05B 17/06 |

\* cited by examiner

APPARATUS FOR GENERATING DRY MIST

CROSS-REFERENCE TO RELATED APPLICATIONS

This application claims the benefit of Provisional Application Ser. No. 63/244,544, filed on Sep. 15, 2021, which is incorporated herein by reference.

TECHNICAL FIELD

The present disclosure relates to airborne mists. More particularly, the present disclosure relates to an apparatus for generating a dry mist.

BACKGROUND

Pathogens, such as bacteria, viruses, mold, and mildew may be easily spread by remaining on surfaces or by passing through the air. Disinfectants have been used to reduce the spread of these pathogens, but their effectiveness is limited. For example, most disinfectants are of a liquid solution and must be either wiped or sprayed onto a surface. Spraying disinfectant into the air, via an applicator, is not effective as the droplets fall to the ground and surface much too fast due to the droplet size and weight. As a result, current disinfectants are inadequate for neutralizing airborne pathogens. Additionally, disinfectant sprays and solutions leave surfaces wet, which is not ideal and may not be safe for many surfaces, such as those with electronics. Disinfectant sprays and sprayers on the market typically do not achieve a micron size smaller than 10. As a result, the droplets are subject to gravity and will burst when landing on a surface, creating a wet spot. As a result, users must typically wipe the surfaces after using these sprayers.

Liquid droplets for cleaning may be separated into 3 major groups:

First, there are the 50 micron and larger droplets that are produced from hand-pump sprayers. Due to their size and mass, gravity pulls them down to the surface. This liquid must then be wiped, spread, or dried after the application. Typical spray glass and bathroom cleaners are examples.

Second, there are 10-50 micron droplets that come from high pressure sprayers with ultra-small orifices in the nozzle. Utilizing hundreds of pounds per square inch pressure, the liquid is forced through these small orifices to break the liquid into small droplets. While these are much smaller than the above-mentioned droplets, they also are subject to gravity and will be pulled down to surfaces and the droplet will "burst" on impact and become a wet spot. As with the above, drying, wiping, and spreading the liquid will be required.

Third, there are 1-9 micron droplets (referred to as dry mist) that are produced by ultrasonic transducers vibrating thousands of times per second. The ultrasonic transducer produces water droplets in all sizes from 1-200 microns. However, 1-9 micron size droplets are not influenced by gravity and remain suspended for hours and/or days based on heat and humidity.

Accordingly, there is a need for a dry mist (e.g., 1-9 micron droplets) disinfectant. In other words, there is a need for a disinfectant that can remain airborne for a significant amount of time, that may penetrate small spaces, and that does not leave surfaces wet. Additionally, there is a need for an apparatus that may produce this dry mist that is not susceptible to corrosion and other component failures. Current dry mist chambers and foggers are designed using metal components, which will not withstand prolonged exposure to hypochlorous acid (HOCL) and water. Delivering HOCL as a dry-mist disinfectant fog with traditional methods results in rapid failure of the metal parts in sprayers, nozzles, chambers, and pumps. Further, the mist expelled needs to be 9 microns and smaller, and ideally less than 4 microns, which has not been consistently achieved using the prior art. While examples are used above that demonstrate the need for dry mist disinfectants, it will be appreciated that the invention is not limited to disinfectant applications. For example, non-disinfectant dry mist (e.g., water) is also needed in plant growth, humidification, and other industries. Accordingly, the present disclosure seeks to solve these and other problems.

SUMMARY OF EXAMPLE EMBODIMENTS

In some embodiments, a dry mist generating apparatus comprises a plastic housing, an ultrasonic transducer, a fan inducing air within the plastic housing, a diffuser plate for controlling direction, velocity, and pressure of the induced air, at least one discharge opening for releasing the resulting dry mist, and a reservoir for capturing droplets that exceed 4 microns. In some embodiments, the ultrasonic transducer is an ultrasonic disc.

In some embodiments, a dry mist generating apparatus further comprises one or more discharge tubes for releasing the dry mist. The length of the tubes may be varied, along with their diameter and angle, to achieve varying micron droplet sizes at discharge.

In some embodiments, a dry mist generating apparatus comprises one or more wheels for easy transportation. In one embodiment, a dry mist generating apparatus may be placed in a cart or carriage.

DETAILED DESCRIPTION OF EXAMPLE EMBODIMENTS

Figure 1:
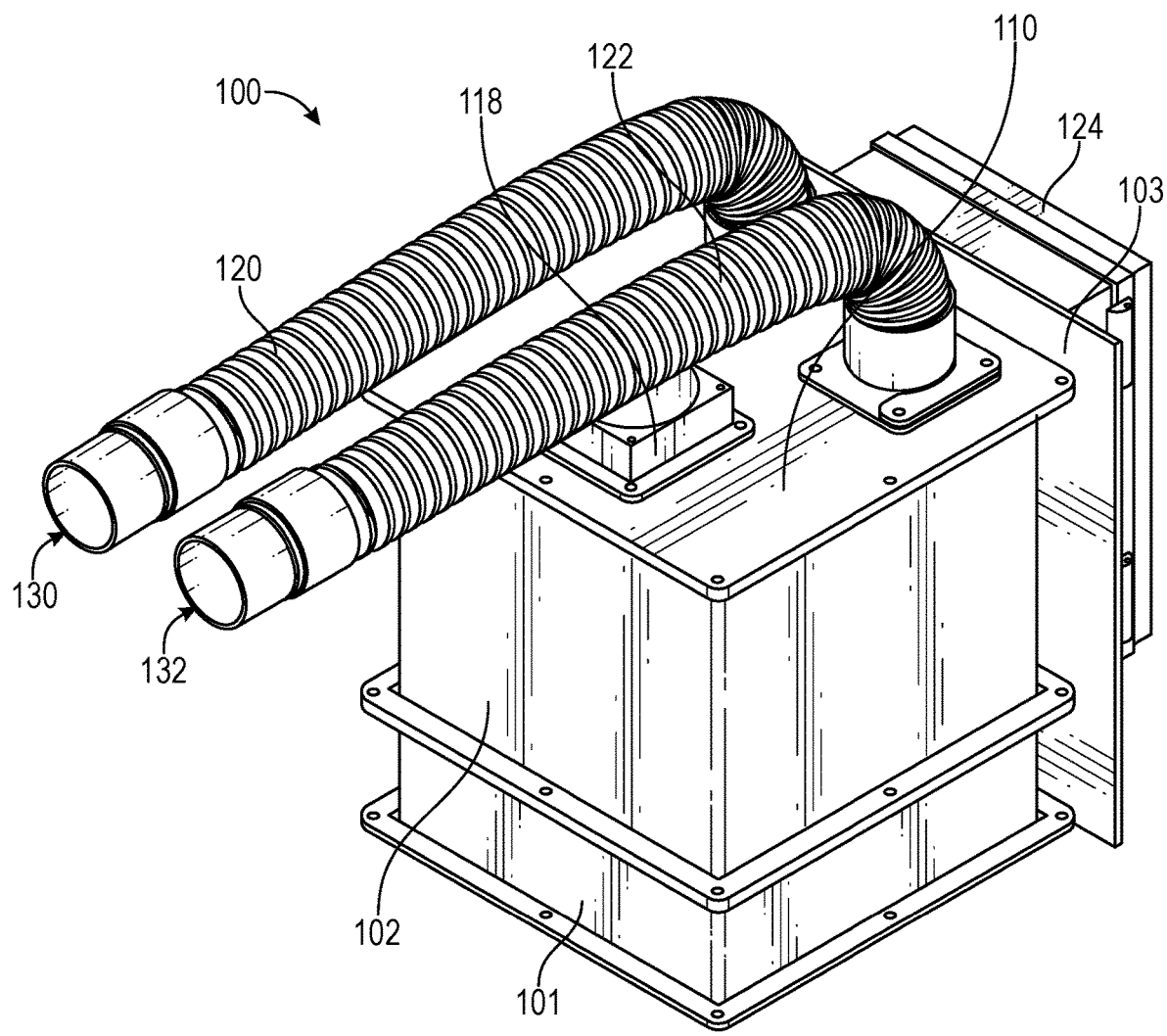
FIG. 1 illustrates a top, front, left perspective view of a dry mist generating apparatus.
Figure 2:
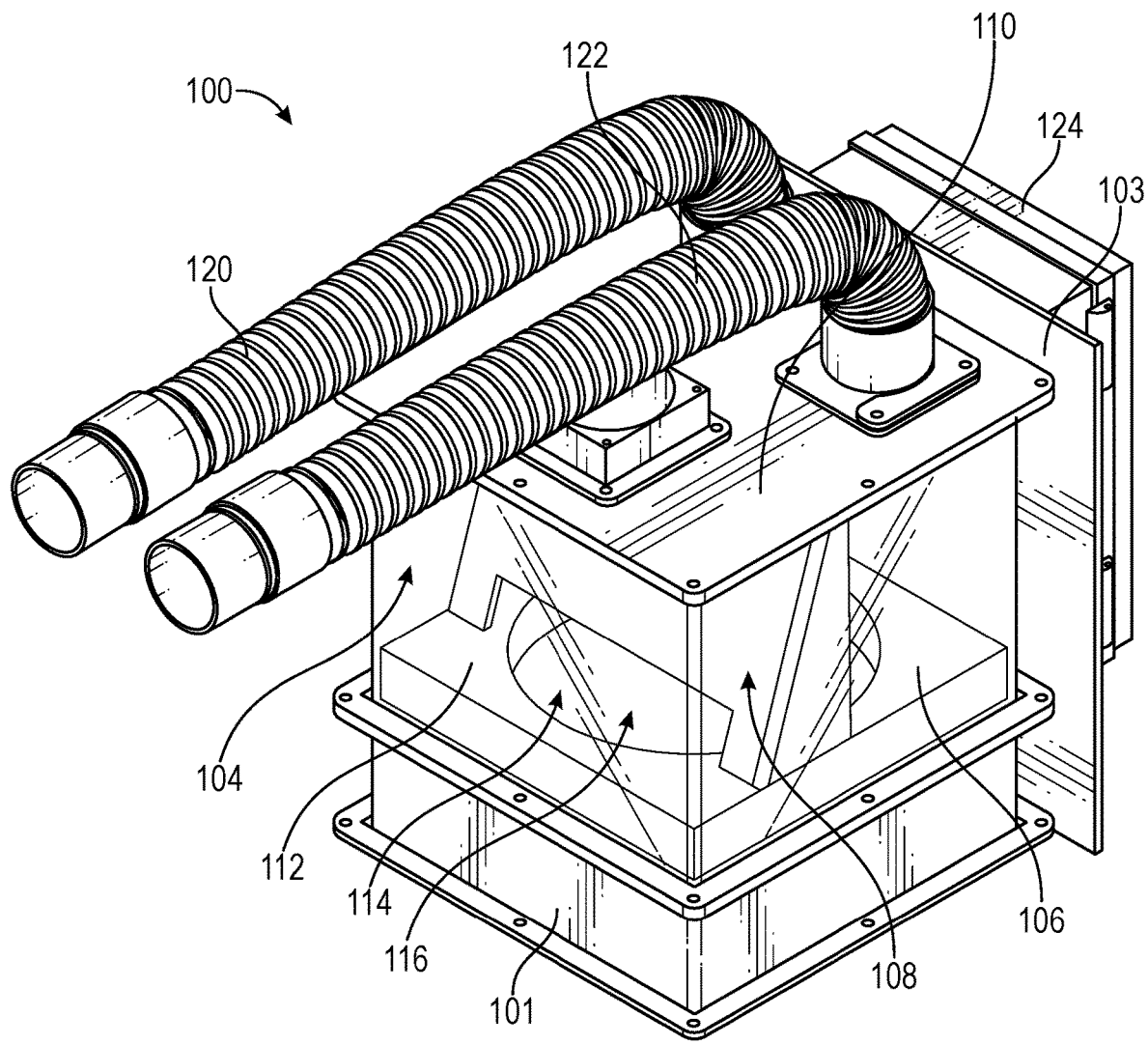
FIG. 2 illustrates a top, front, left perspective view of a dry mist generating apparatus with a transparent housing for ease of viewing internal components.
Figure 3:
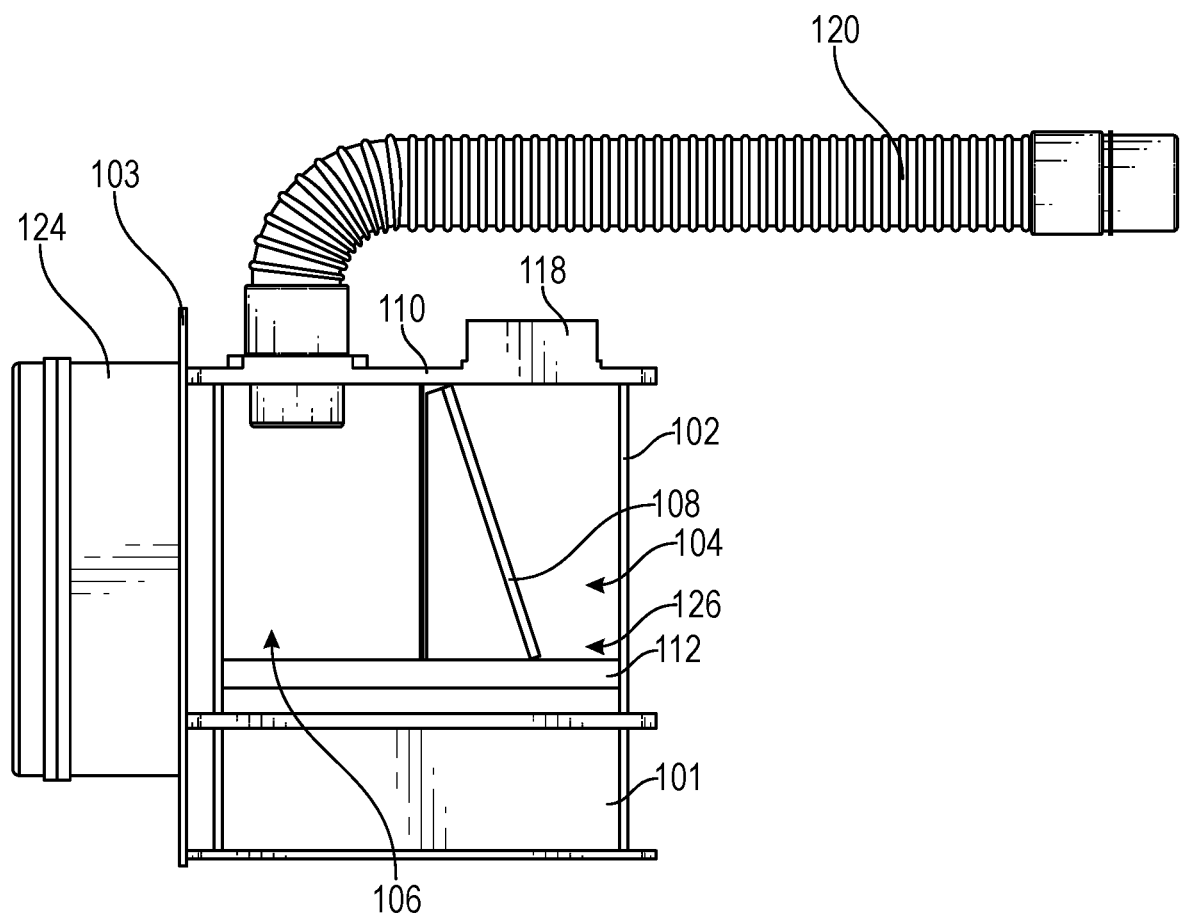
FIG. 3 illustrates a right side elevation view.
Figure 4:
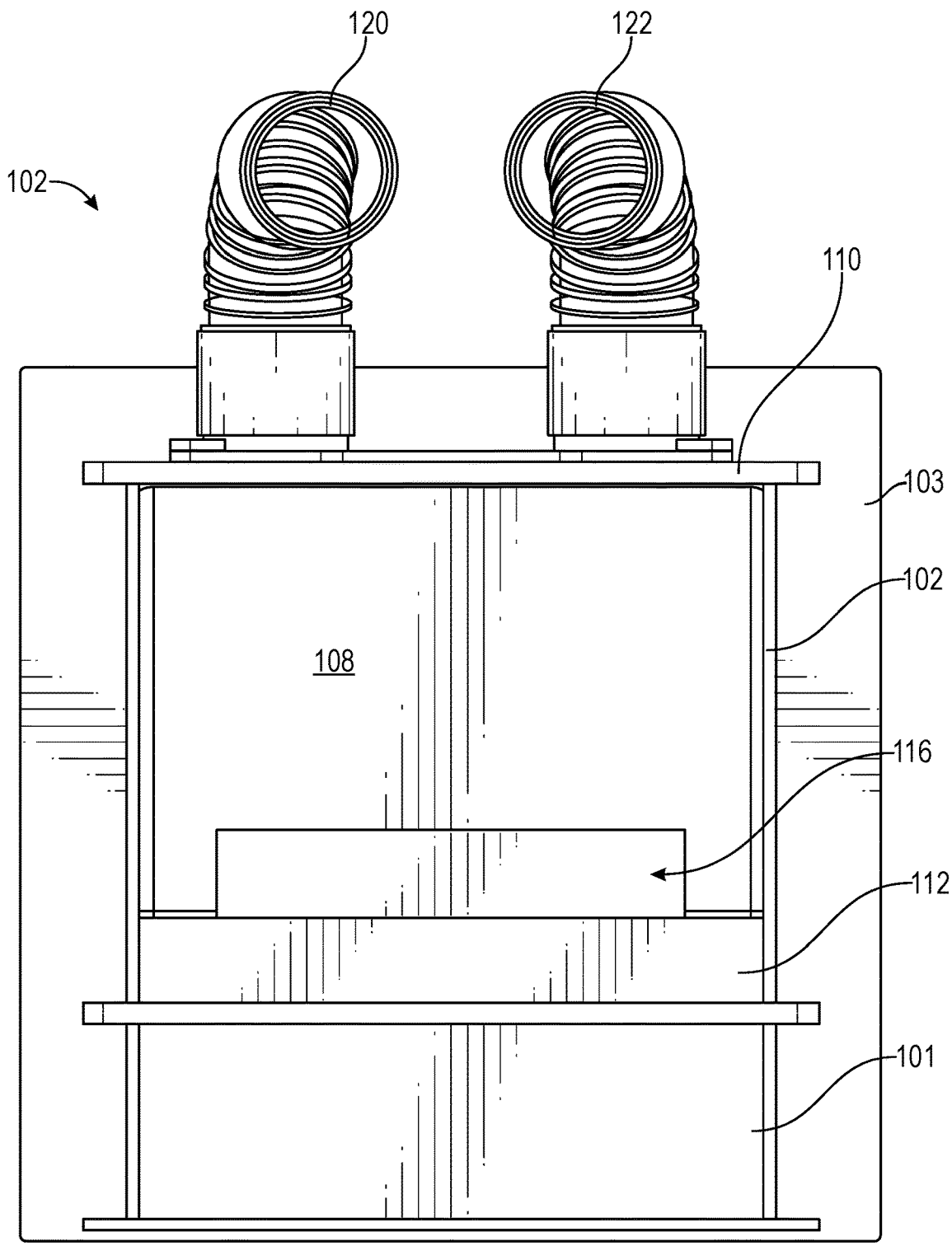
FIG. 4 illustrates a front elevation view of a dry mist generating apparatus.
Figure 5:
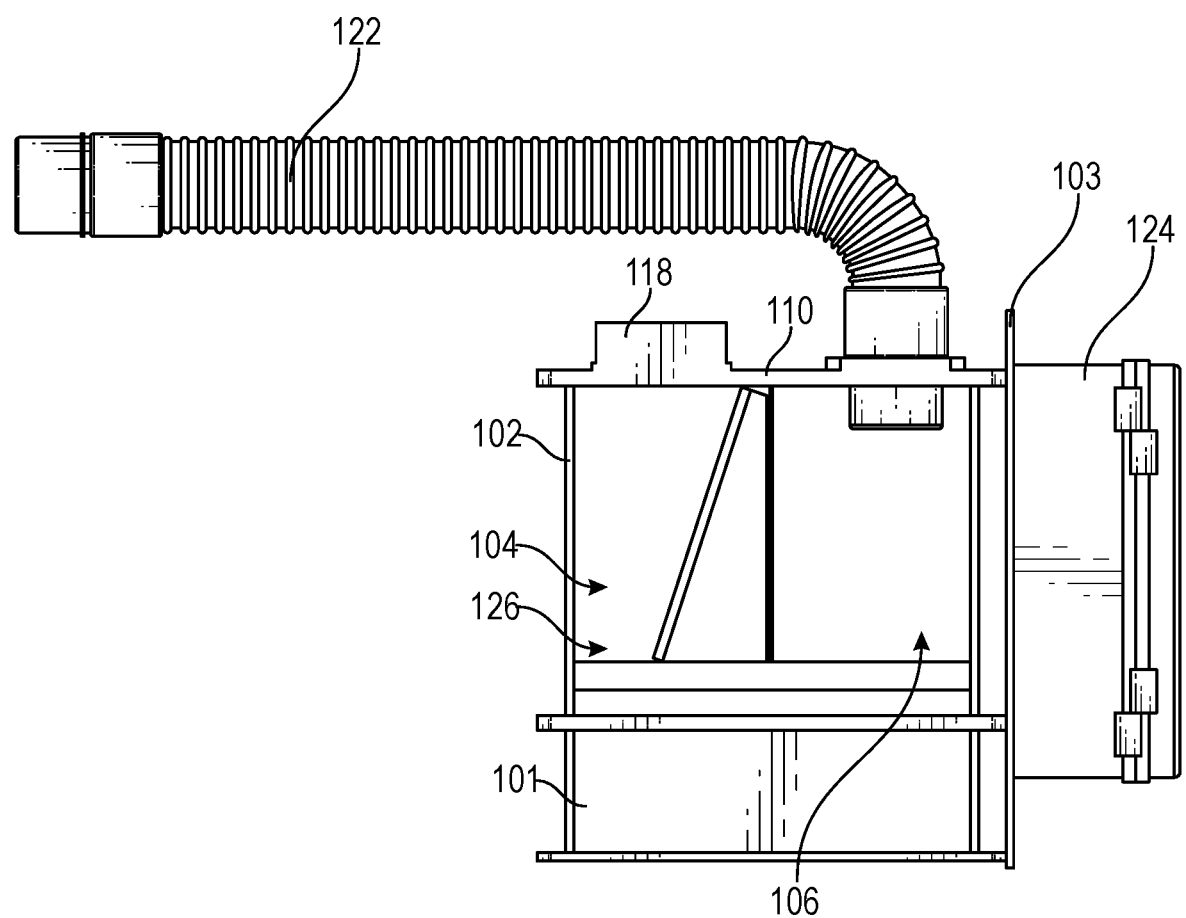
FIG. 5 illustrates a left side elevation view of a dry mist generating apparatus.
Figure 6:
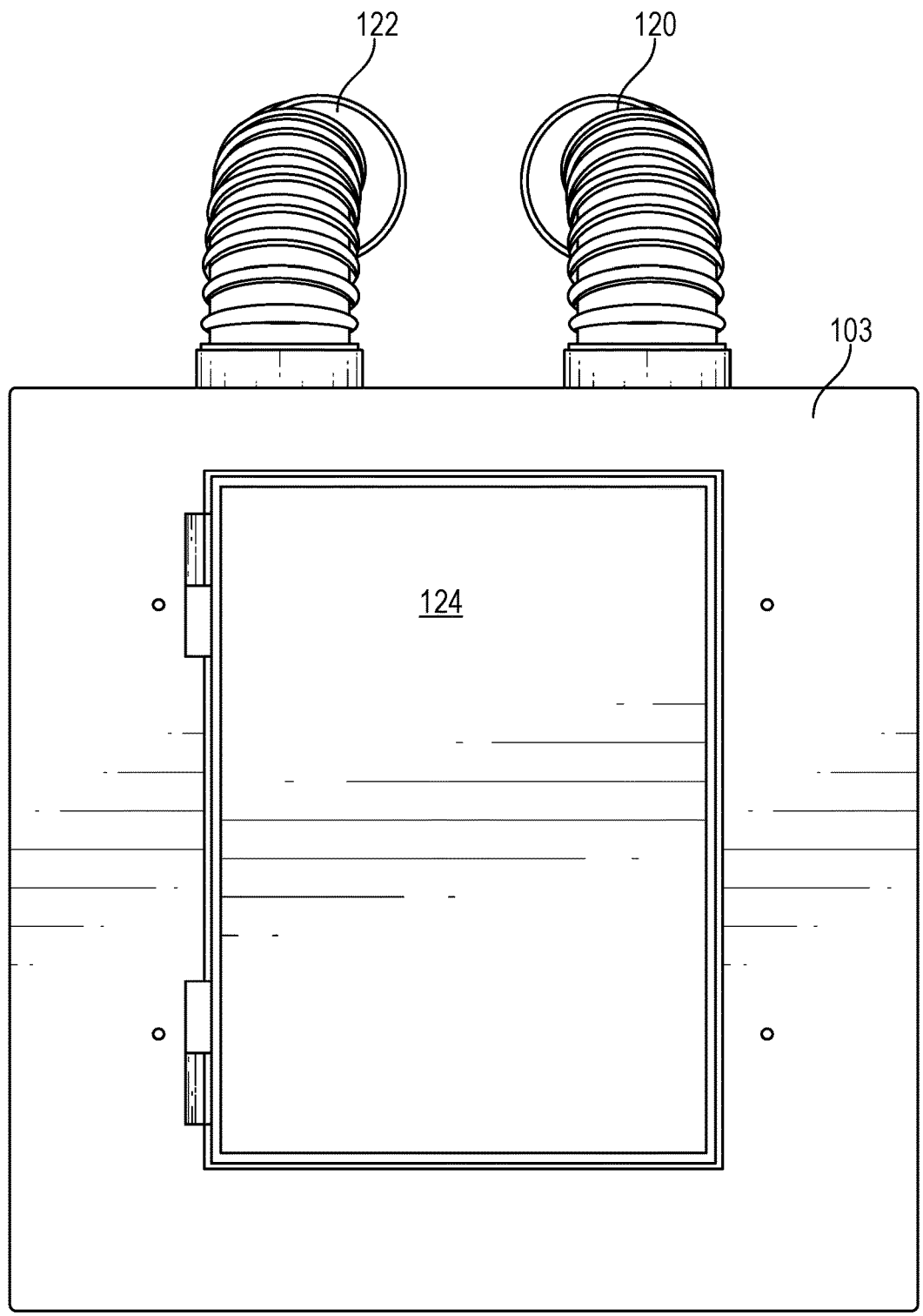
FIG. 6 illustrates a rear elevation view of a dry mist generating apparatus.
Figure 7:
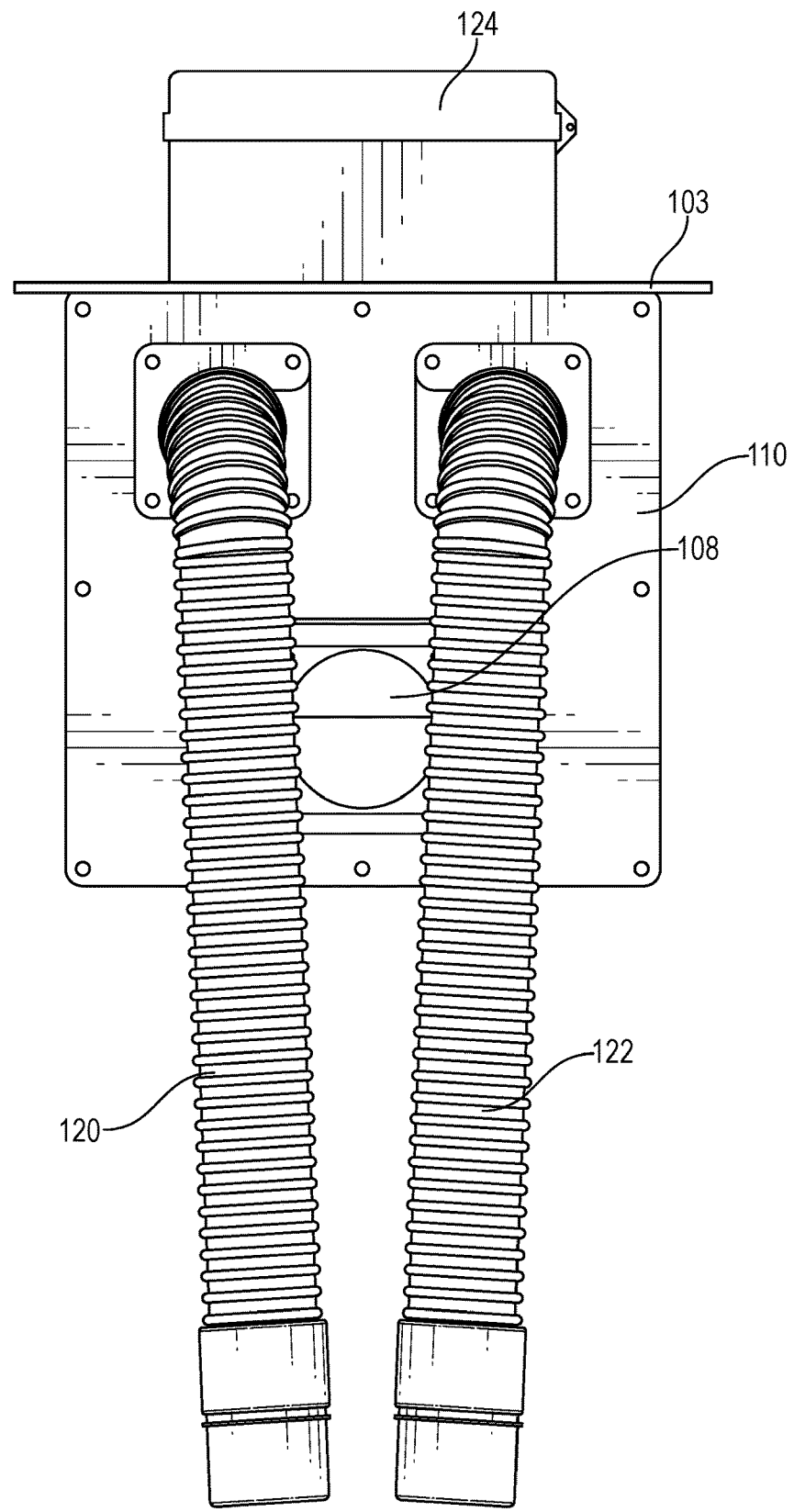
FIG. 7 illustrates a top plan view of a dry mist generating apparatus.

The following descriptions depict only example embodiments and are not to be considered limiting in scope. Any reference herein to "the invention" is not intended to restrict or limit the invention to exact features or steps of any one or more of the exemplary embodiments disclosed in the present specification. References to "one embodiment," "an embodiment," "various embodiments," and the like, may indicate that the embodiment(s) so described may include a particular feature, structure, or characteristic, but not every embodiment necessarily includes the particular feature, structure, or characteristic. Further, repeated use of the phrase "in one embodiment," or "in an embodiment," do not necessarily refer to the same embodiment, although they may.

Reference to the drawings is done throughout the disclosure using various numbers. The numbers used are for the convenience of the drafter only and the absence of numbers in an apparent sequence should not be considered limiting and does not imply that additional parts of that particular embodiment exist. Numbering patterns from one embodiment to the other need not imply that each embodiment has similar parts, although it may.

Accordingly, the particular arrangements disclosed are meant to be illustrative only and not limiting as to the scope of the invention, which is to be given the full breadth of the appended claims and any and all equivalents thereof. Although specific terms are employed herein, they are used in a generic and descriptive sense only and not for purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. When used herein to join a list of items, the term "or" denotes at least one of the items, but does not exclude a plurality of items of the list. For exemplary methods or processes, the sequence and/or arrangement of steps described herein are illustrative and not restrictive.

It should be understood that the steps of any such processes or methods are not limited to being carried out in any particular sequence, arrangement, or with any particular graphics or interface. Indeed, the steps of the disclosed processes or methods generally may be carried out in various sequences and arrangements while still falling within the scope of the present invention.

The term "coupled" may mean that two or more elements are in direct physical contact. However, "coupled" may also mean that two or more elements are not in direct contact with each other, but yet still cooperate or interact with each other.

The terms "comprising," "including," "having," and the like, as used with respect to embodiments, are synonymous, and are generally intended as "open" terms (e.g., the term "including" should be interpreted as "including, but not limited to," the term "having" should be interpreted as "having at least," the term "includes" should be interpreted as "includes, but is not limited to," etc.).

Figure 12:
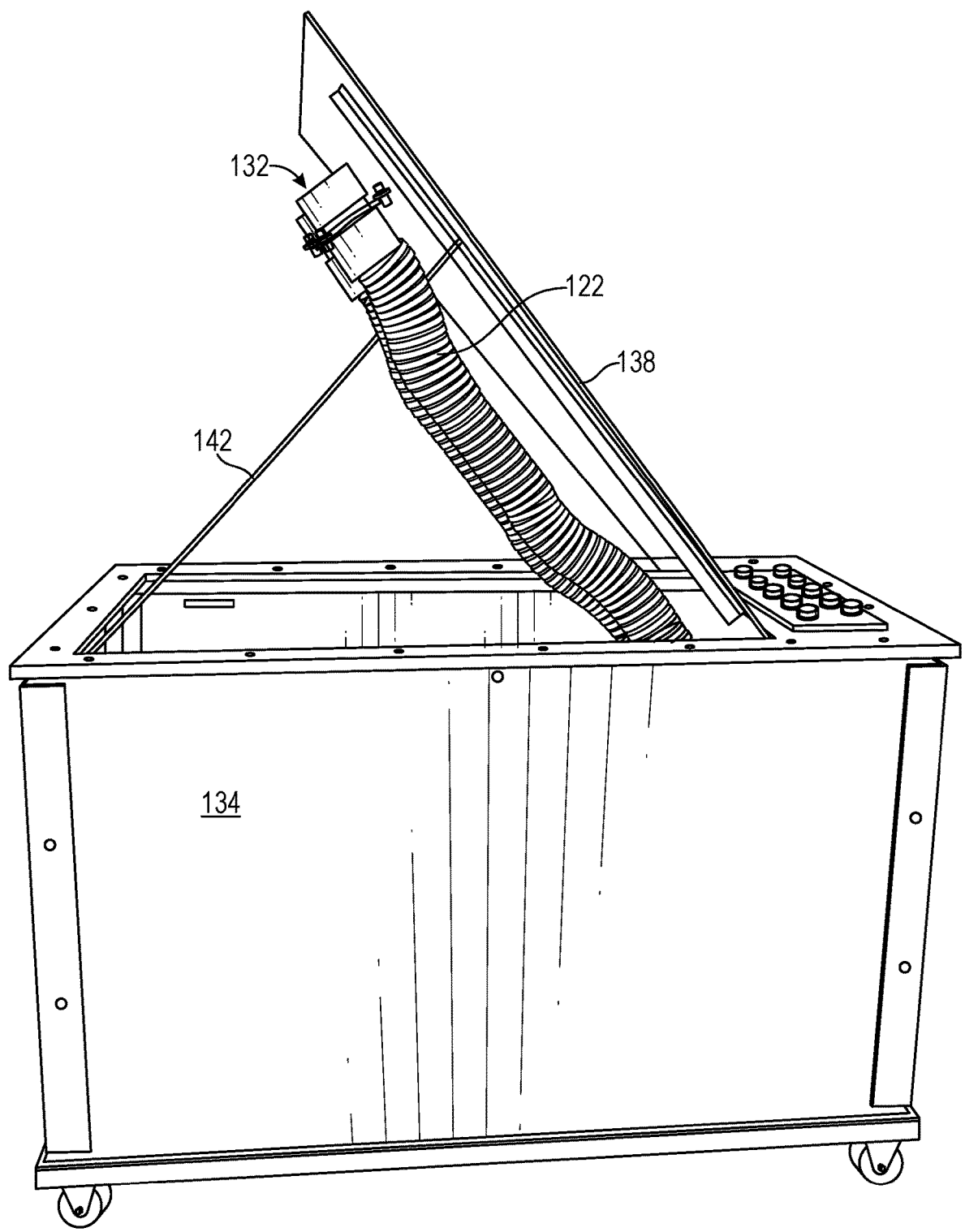
FIG. 12 illustrates a top, left side perspective view of a dry mist generating apparatus.
Figure 13:
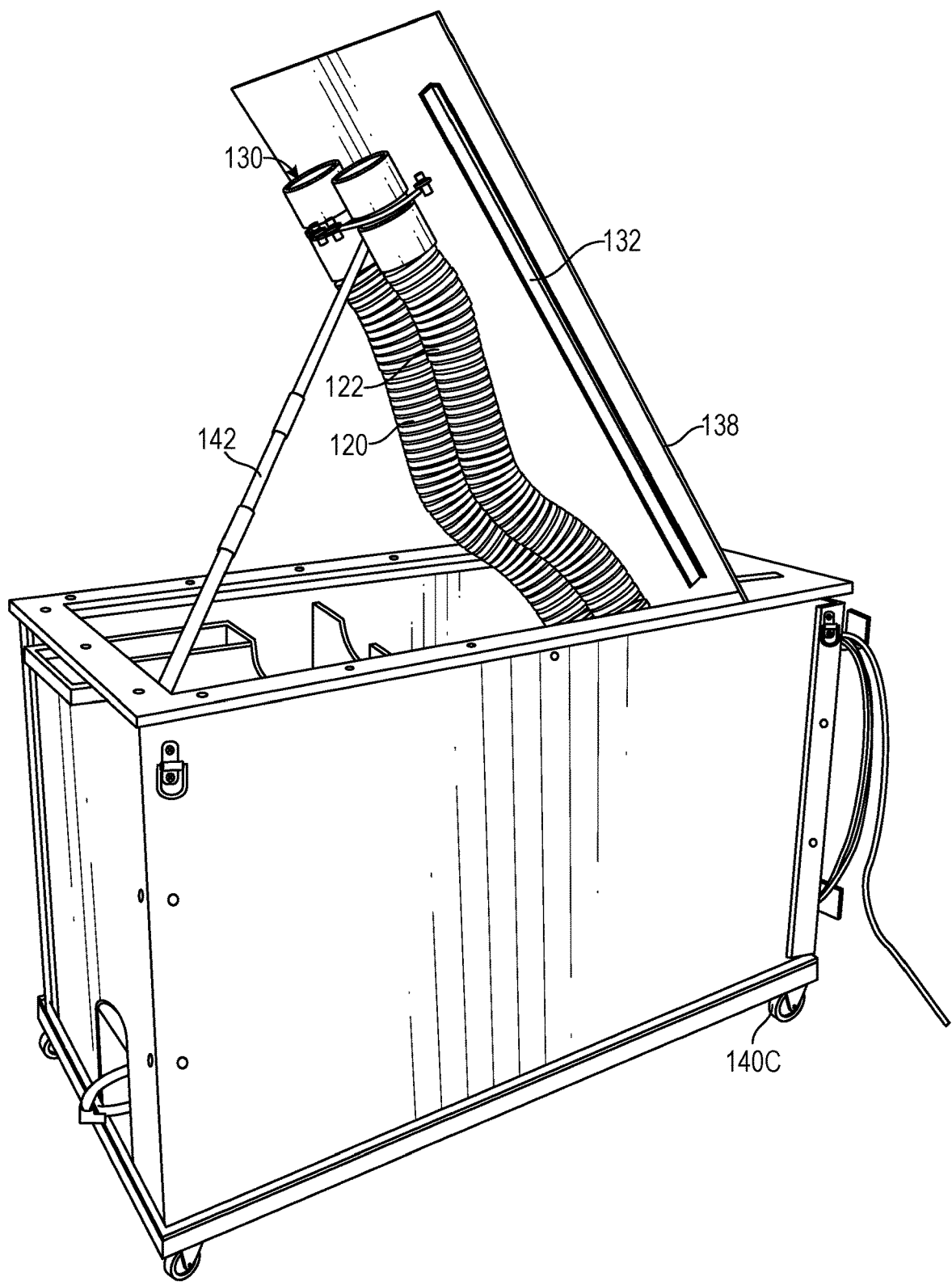
FIG. 13 illustrates a top, front, left side perspective view of a dry mist generating apparatus.
Figure 14:
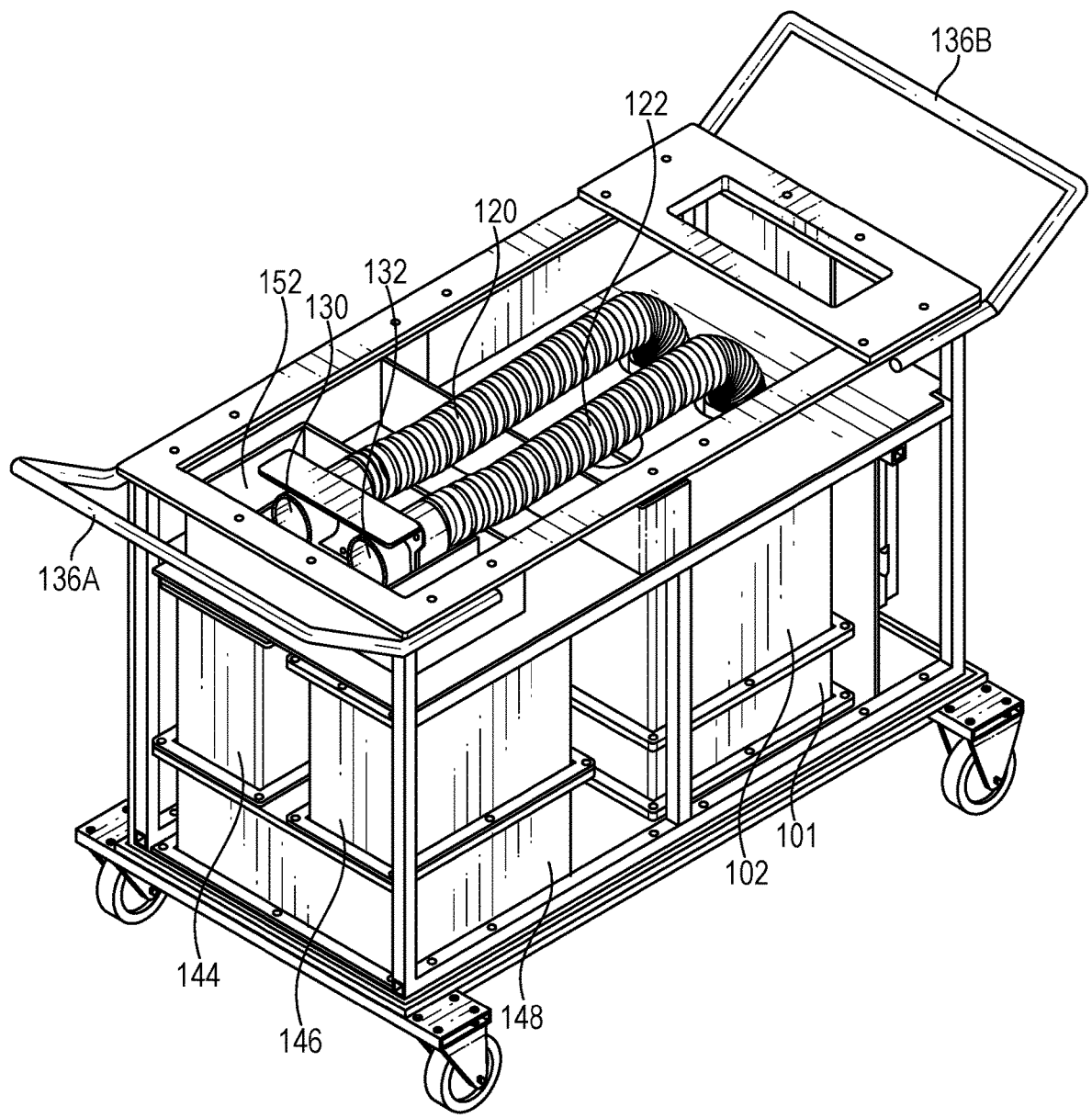
FIG. 14 illustrates a top, front, left side perspective view of a dry mist generating apparatus with the sidewalls of a cart removed for ease of viewing interior components.
Figure 15:
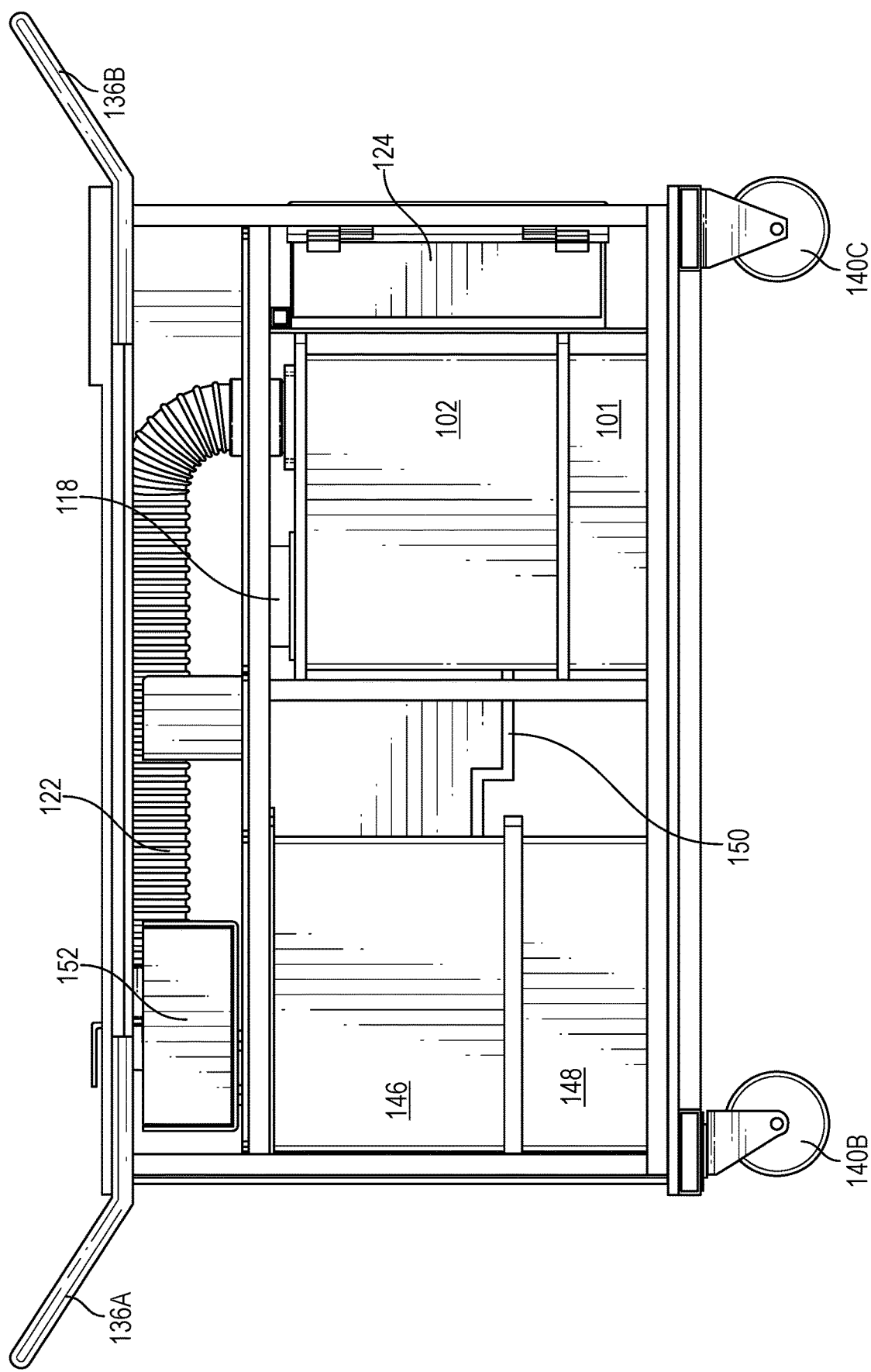
FIG. 15 illustrates a left side elevation view of a dry mist generating apparatus.
Figure 16:
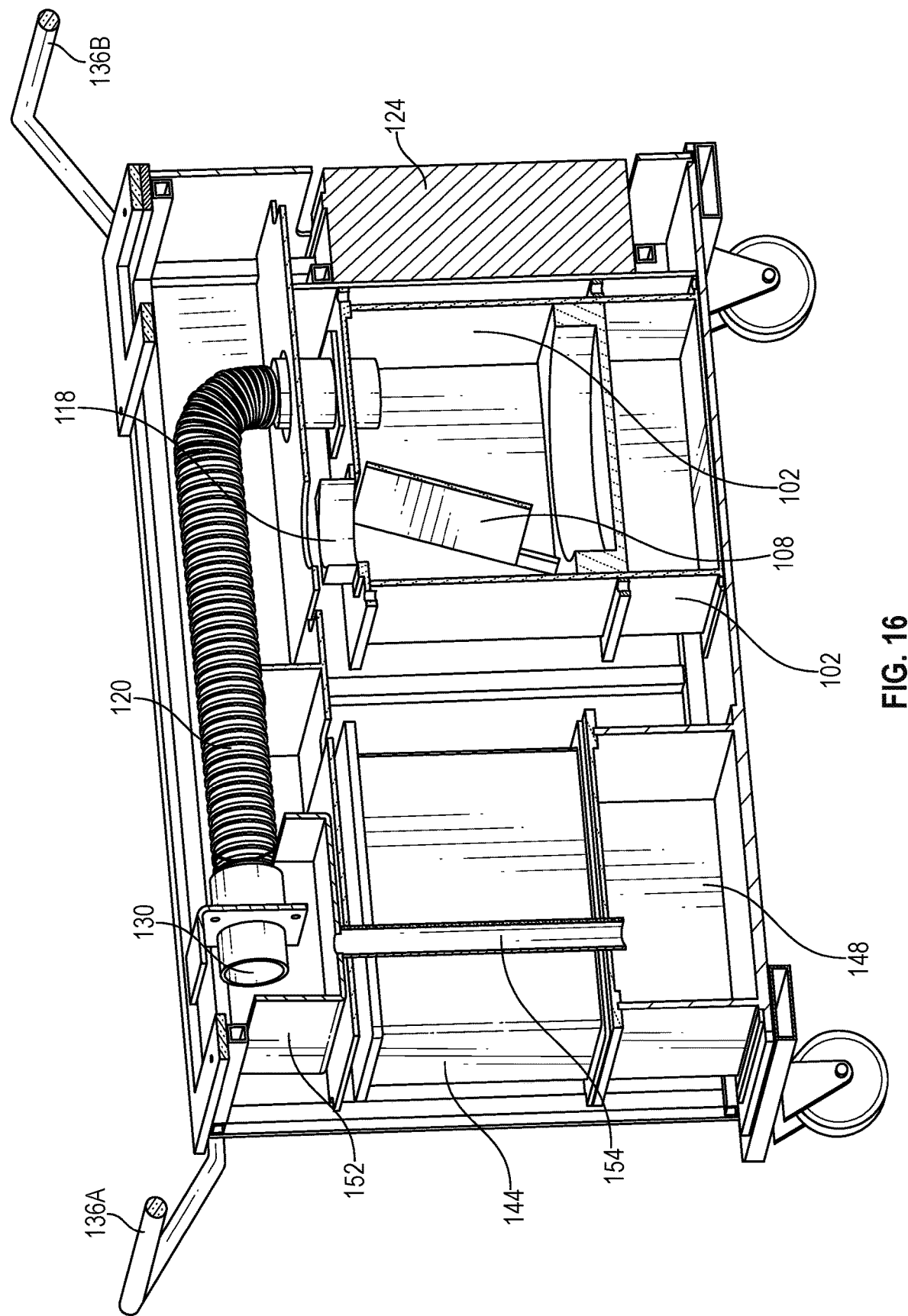
FIG. 16 illustrates a longitudinal cross-section of a dry mist generating apparatus.
Figure 17:
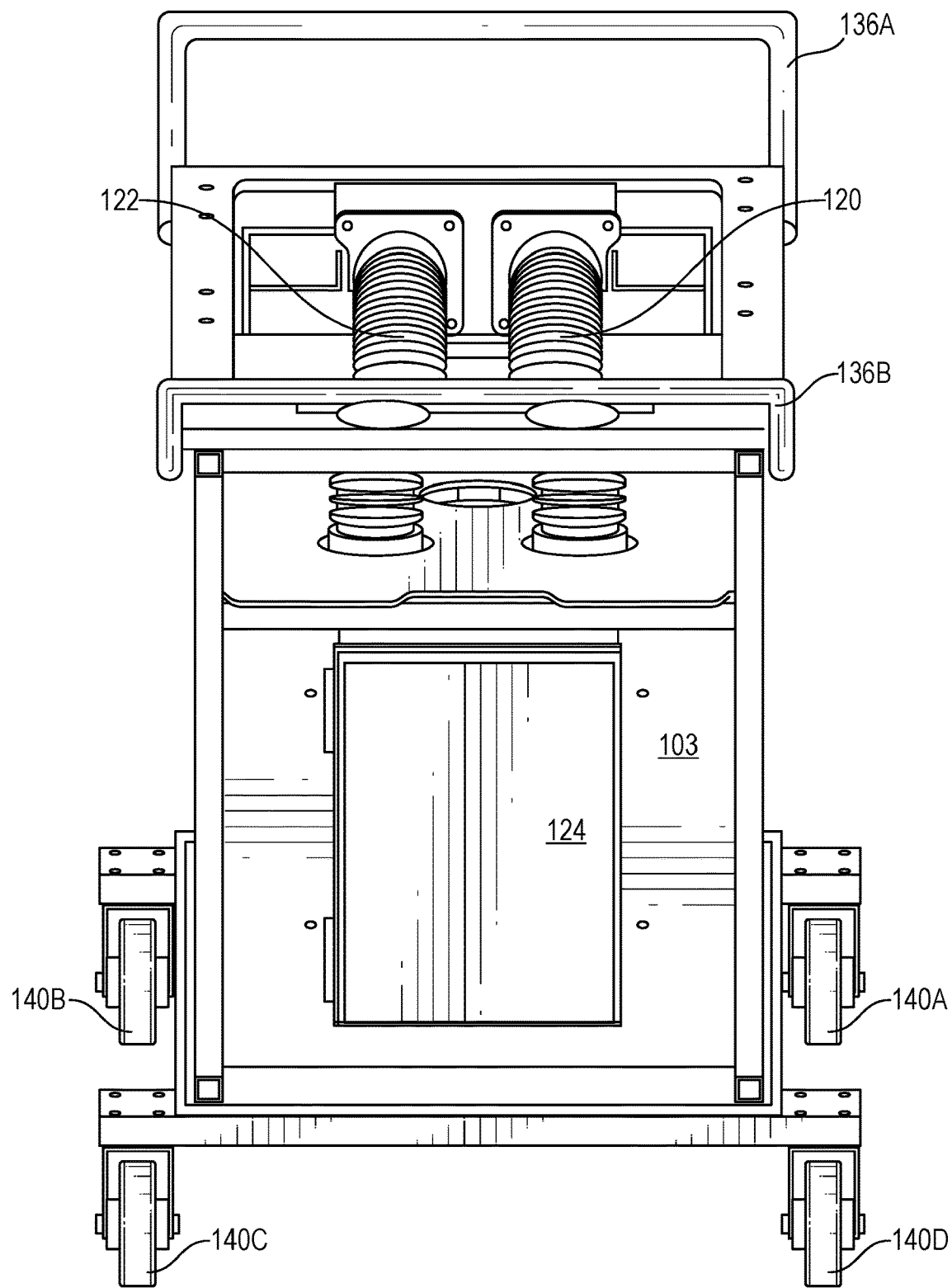
FIG. 17 illustrates a top, rear perspective view of a dry mist generating apparatus.
Figure 18:
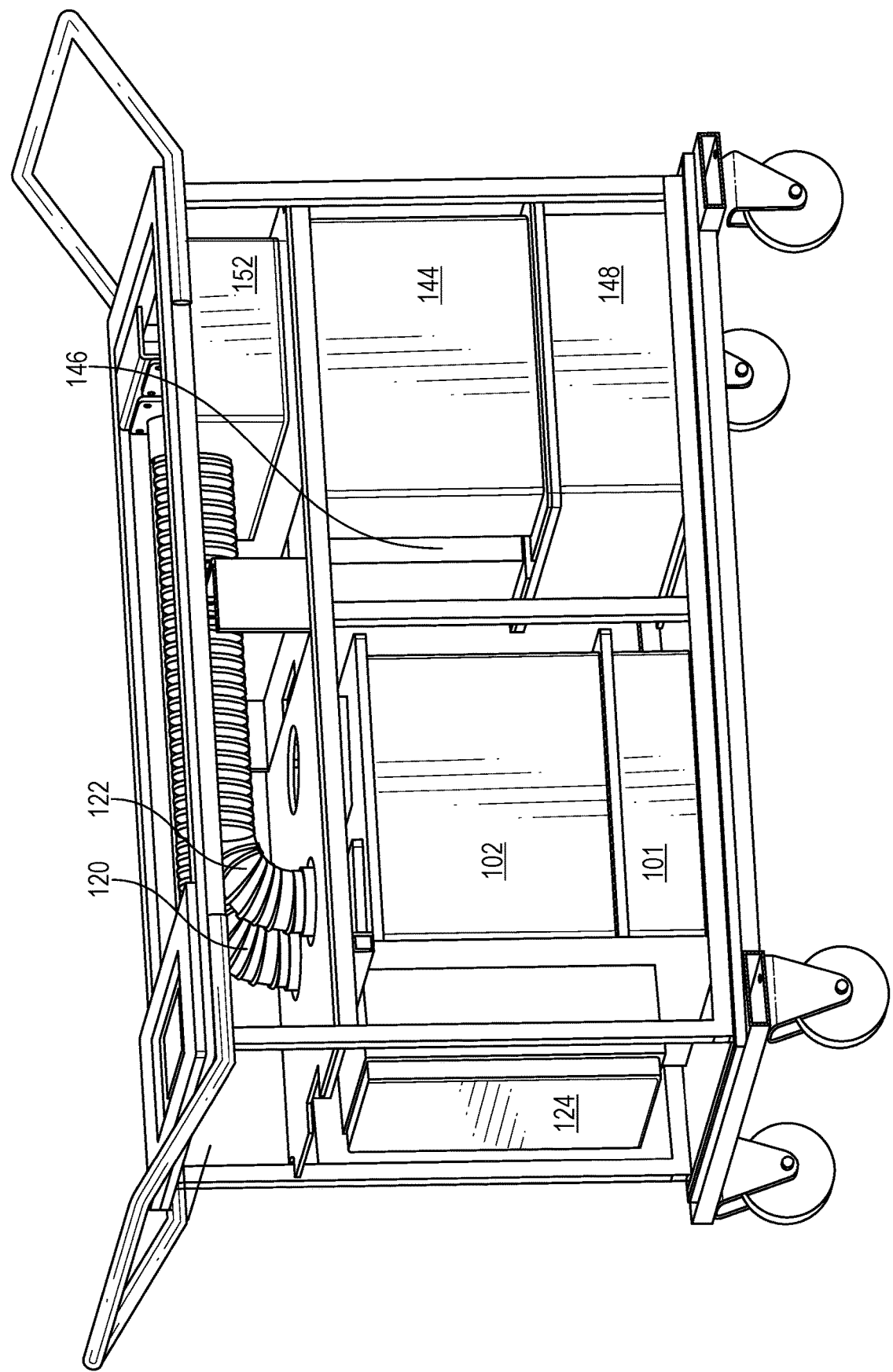
FIG. 18 illustrates a top, front, right side perspective view of a dry mist generating apparatus.
Figure 19:
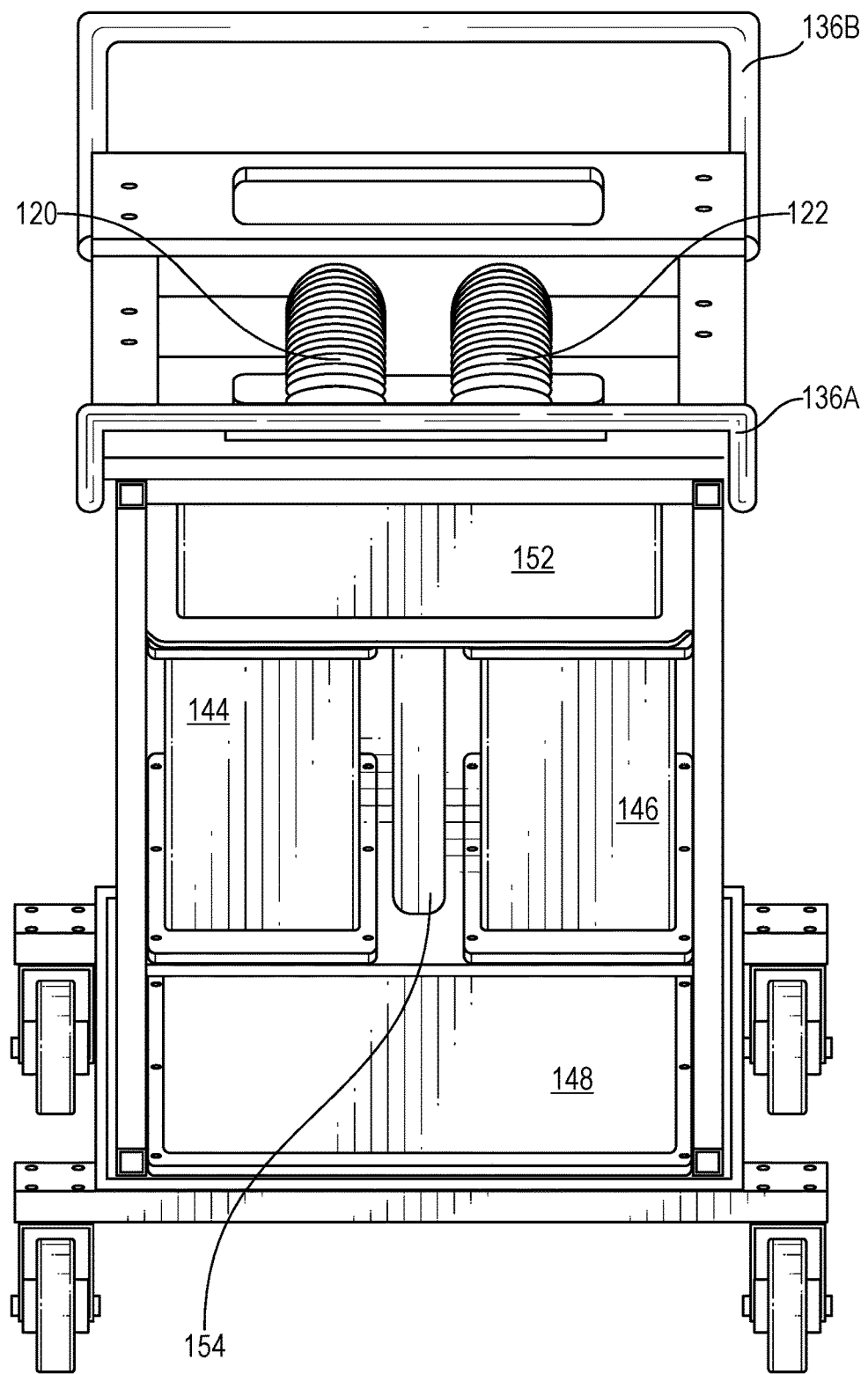
FIG. 19 illustrates a front, top perspective view of a dry mist generating apparatus.
Figure 20:
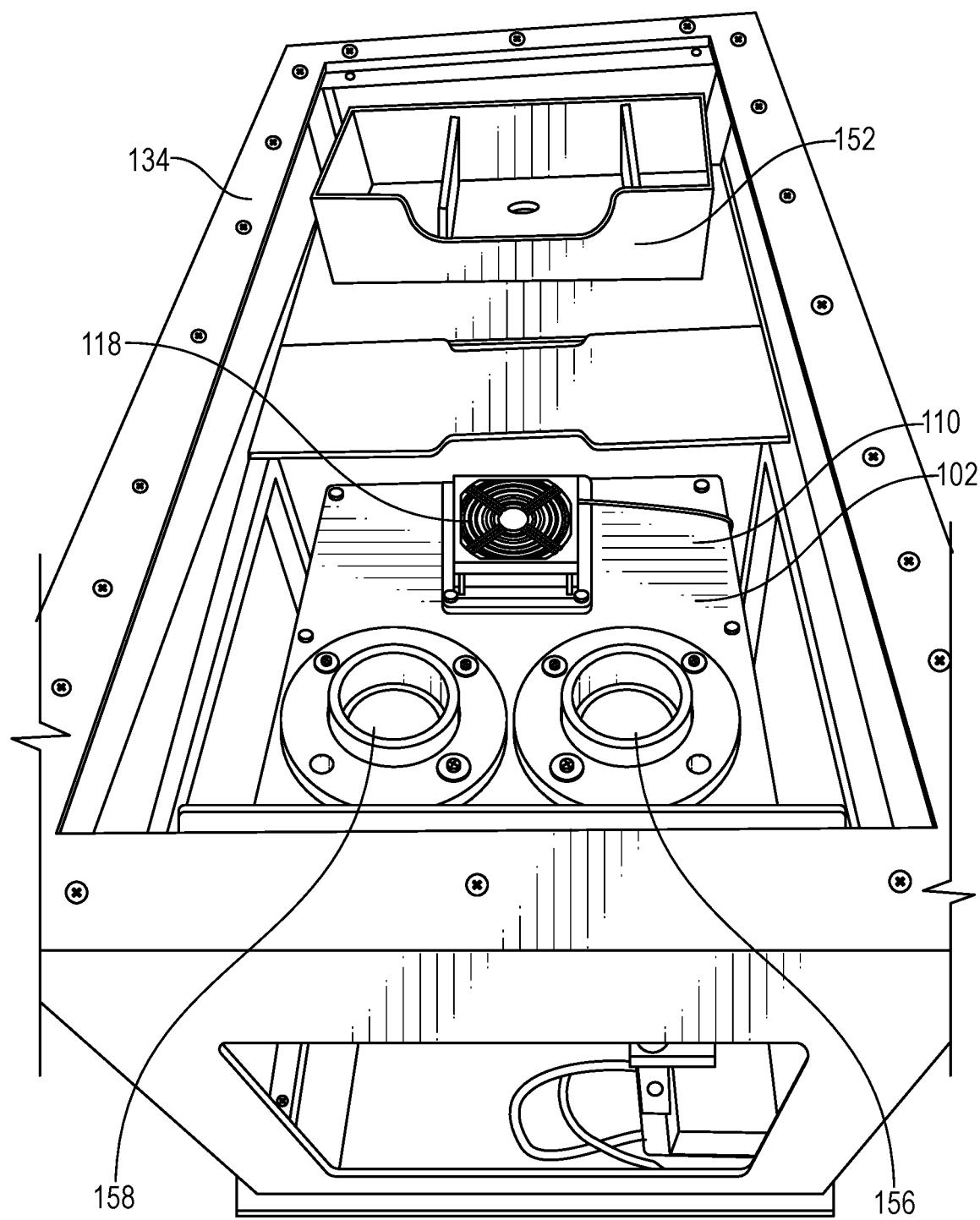
FIG. 20 illustrates a detailed, top perspective view of a dry mist generating apparatus with a lid removed.
Figure 21:
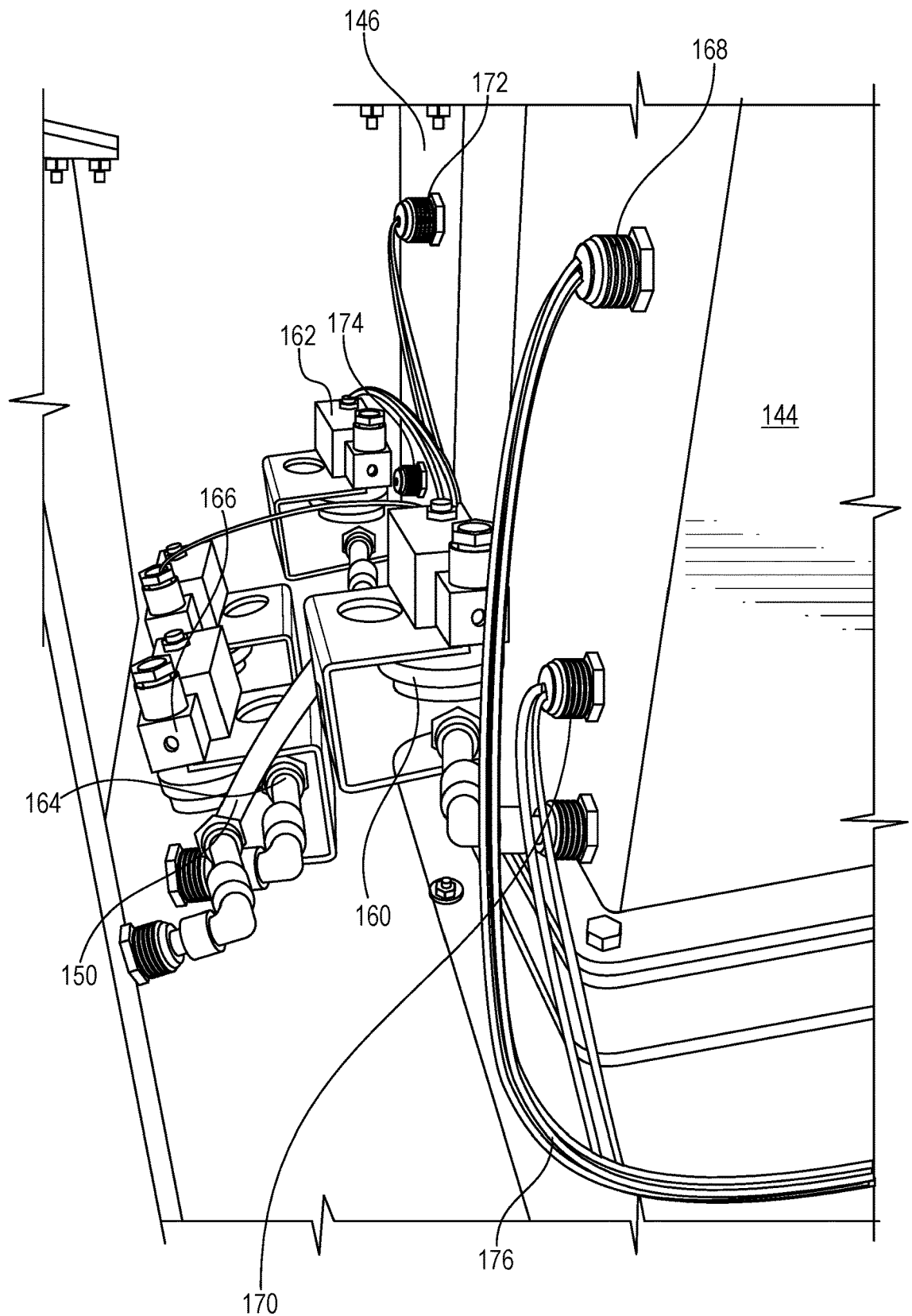
FIG. 21 illustrates a detailed perspective view of pipes, valves, and sensors of a dry mist generating apparatus.
Figure 22:
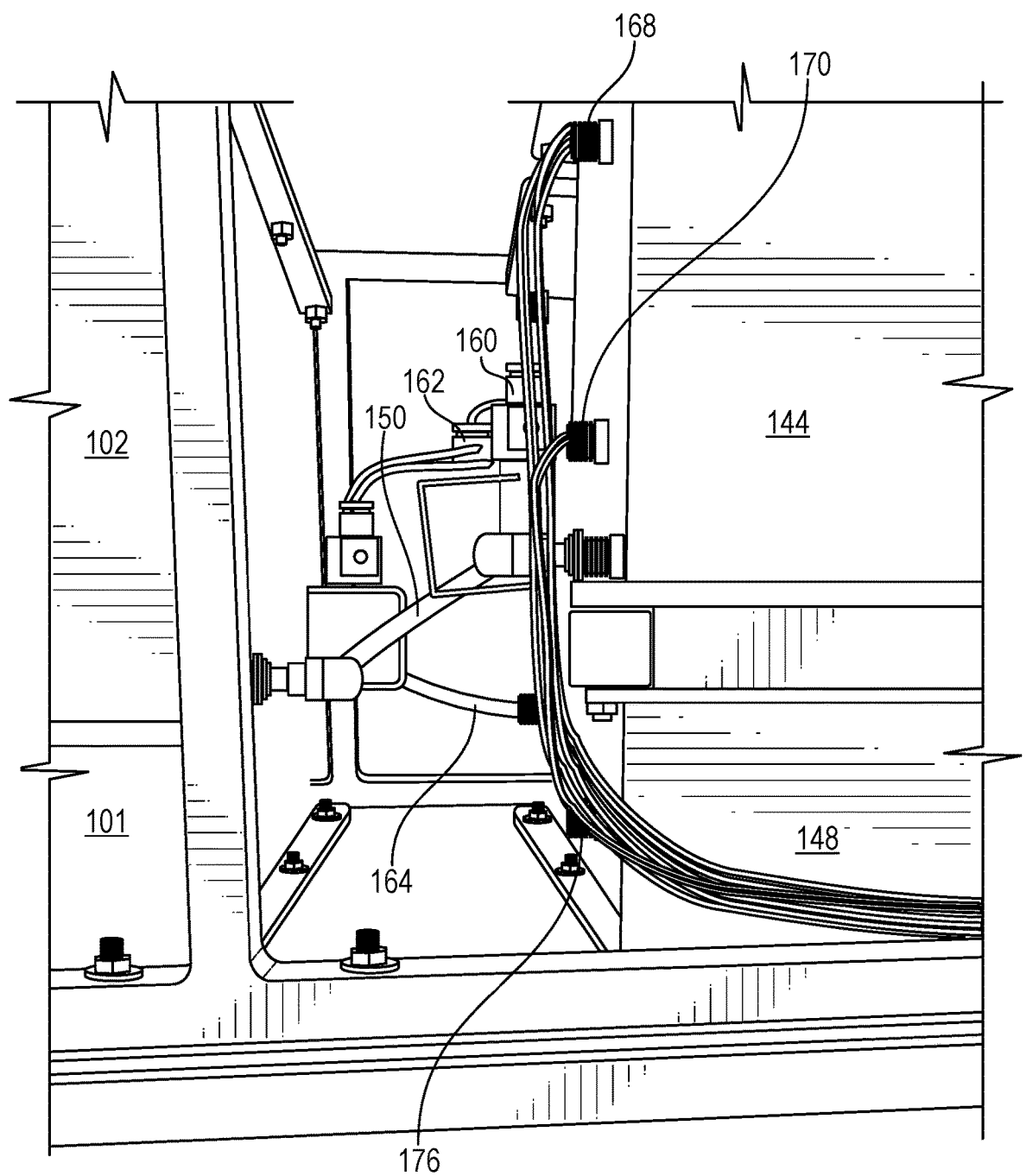
FIG. 22 illustrates a detailed perspective view of pipes, valves, and sensors of a dry mist generating apparatus.
Figure 23:
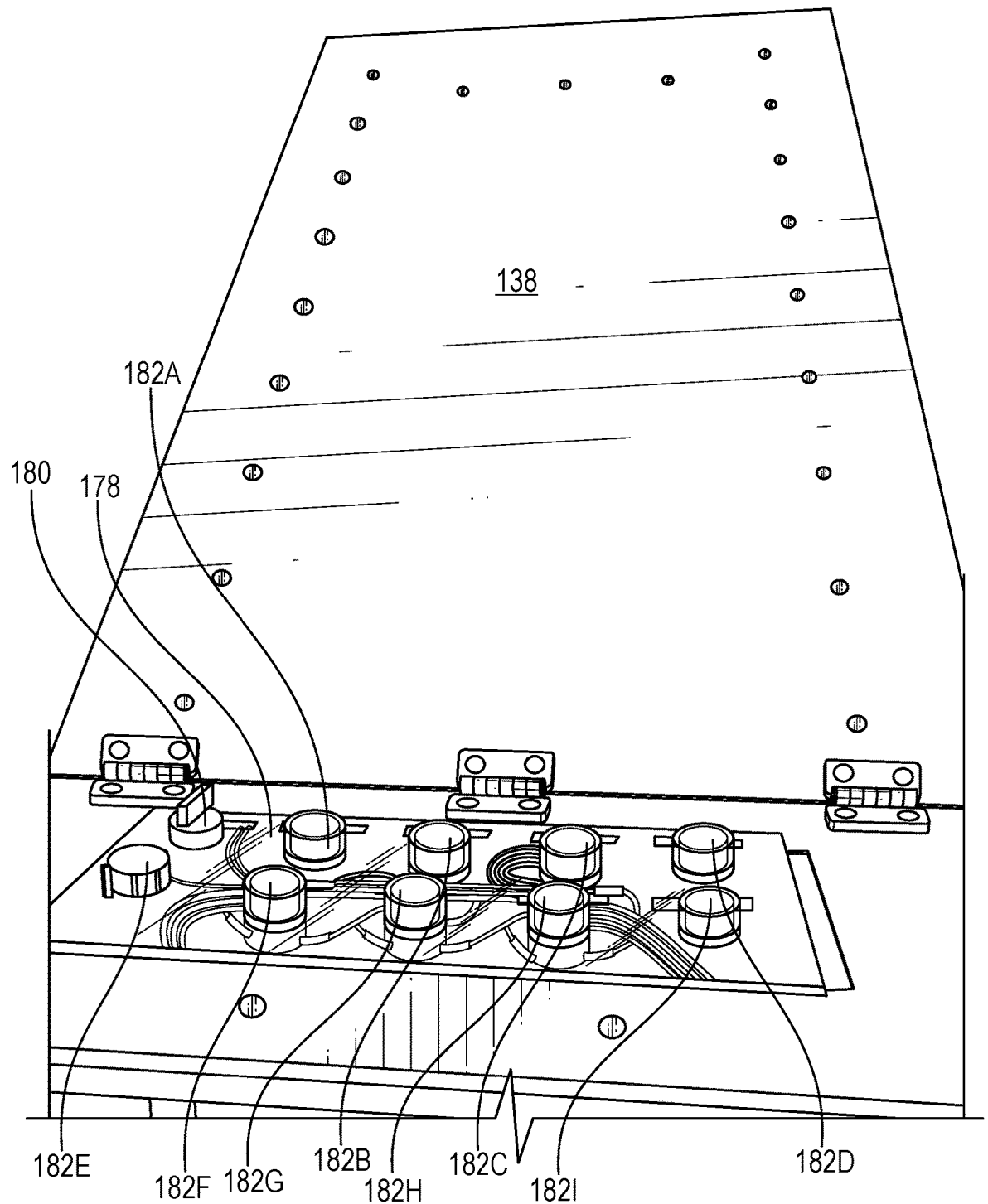
FIG. 23 illustrates a rear detailed perspective view of a dry mist generating apparatus with a lid in an open position.
Figure 24:
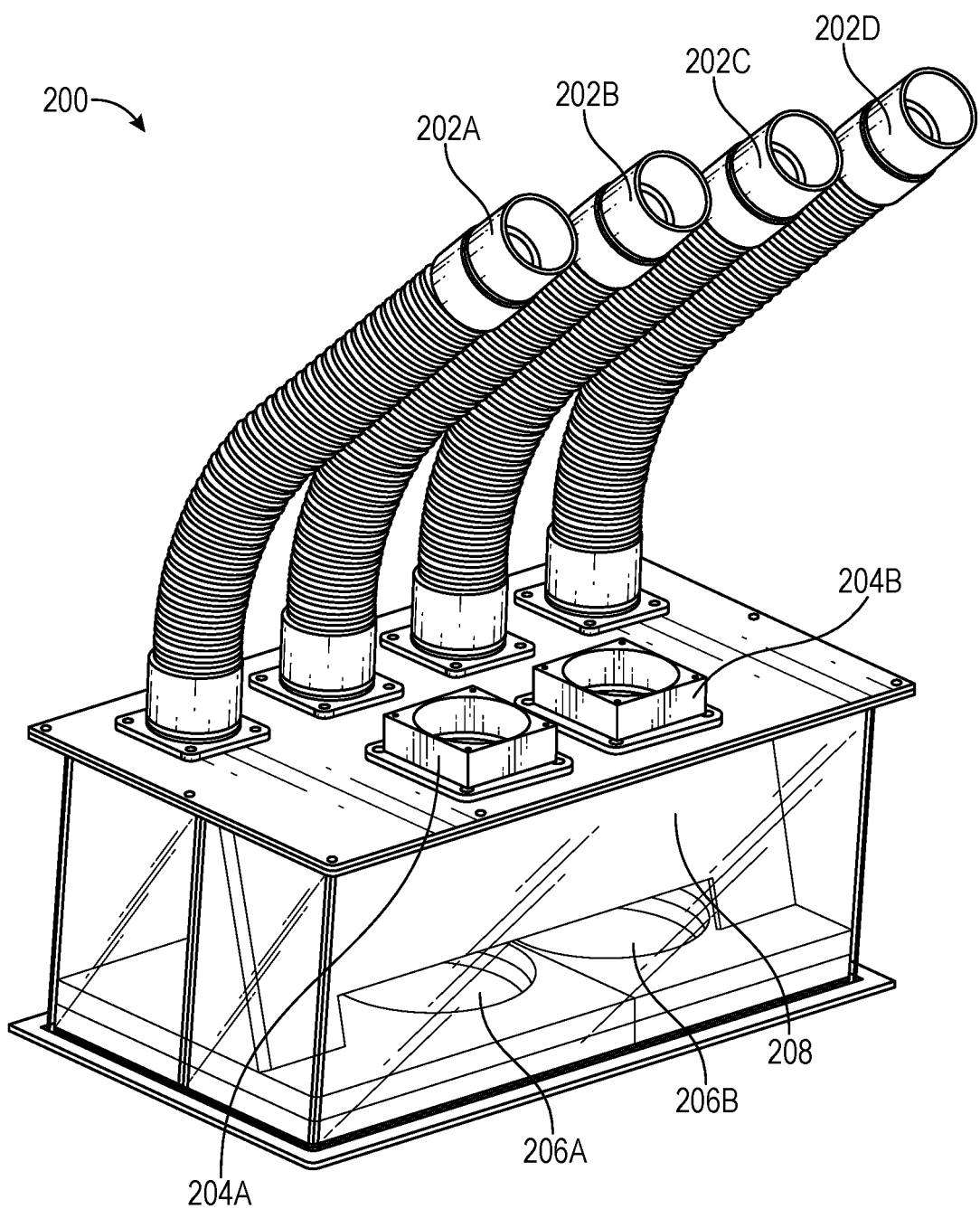
FIG. 24 illustrates a top, right side, front perspective view of a dry mist generating apparatus.
Figure 25:
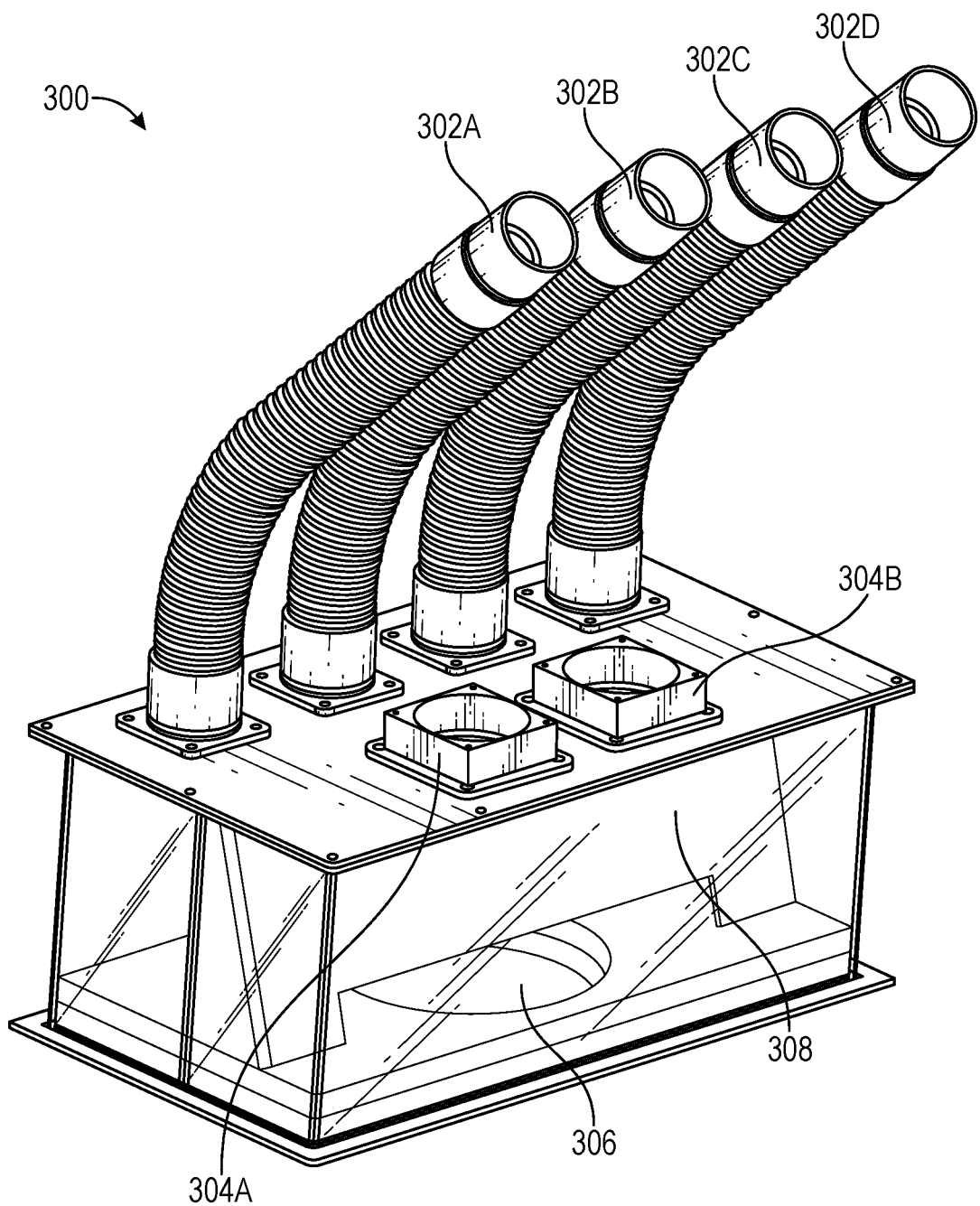
FIG. 25 illustrates a top, right side, front perspective view of a dry mist generating apparatus.

As previously discussed, there is a need for a mist that can remain airborne for a significant amount of time, that may penetrate small spaces, and that does not leave surfaces wet, which may be useful in a variety of industries, including, but not limited to, disinfecting, humidifying, plant growth, etc. Additionally, there is a need for an apparatus that may produce this dry mist that is not susceptible to corrosion and other component failures. The apparatus for generating dry mist disclosed herein solves these and other problems.

In some embodiments, as shown in FIGS. 1-10, a dry mist generating apparatus 100 comprises a plastic housing 102 having a first chamber 104 and a second chamber 106 separated by a diffuser plate 108. As shown, the diffuser plate 108 is non-perpendicular (e.g., angled 45 degrees) to a top 110 and a base 112 of housing 102. The base 112 comprises an ultrasonic transducer (e.g., ultrasonic disc) aperture 114 configured to receive an ultrasonic transducer 115 (best seen in FIGS. 8 & 10). The diffuser plate 108 comprises an air aperture 116 near the base 112 and straddling the ultrasonic transducer aperture 114 that allows for the passage of air and mist from the first chamber 104 to the second chamber 106. A fan 118 forces air into the top of the first chamber 104 where the diffuser plate 108 directs the air to the lower, front of the first chamber 104 (i.e., a narrow neck 126, FIG. 3). The narrow neck 126 increases the velocity of the air and reduces pressure. The air then passes above the ultrasonic transducer via the air aperture 116 of the diffuser plate 108 and into the second chamber 106. Because of the reduced air pressure when entering the second chamber 106, the air lifts the dry mist (ideally about 3 microns or less, but range from 1-9 microns), which is created by an ultrasonic transducer within aperture 114, to force it out through one or more discharge tubes 120, 122.

Droplets that exceed 4 microns remain in the reservoir (bottom of chambers 104, 106) by condensing and falling back to the chambers 104, 106. For example, liquid is added to the housing 102 where it is then converted to a dry mist via an ultrasonic transducer located at the base of the housing 102. The fan 118 then causes air to flow from the first chamber 104, under the diffuser plate 108, and into the second chamber 106 where it then rises upwardly to exit through the discharge tubes 120, 122 at the top of the housing 102. As the air travels upward to the discharge tubes 120, 122, the dry mist is carried in the air upward and outward through the discharge tubes 120, 122 as well. If any droplets larger than 4 microns happen to enter the discharge tubes 120, 122, the droplets condense on the sides of the tubes and fall back into the second chamber 106. To ensure this occurs, the discharge tubes 120, 122 are, ideally, non-linear. In other words, the discharge tubes 120, 122 have bends that aid in collecting droplets excess in size, as best shown in FIGS. 12-13. This non-linear configuration is most readily achieved using flexible tubing. However, it will be appreciated that non-flexible tubing that is shaped to be non-linear may also be used.

The dry mist generating apparatus 100 further comprises a controller 124 (e.g., microcontroller) which may be coupled to the housing 102 via a mounting plate 103. The controller 124 is configured to control the power status of the dry mist generating apparatus 100, as well as monitor various components of the dry mist generating apparatus 100, as will be discussed in greater detail later herein.

Figure 8:
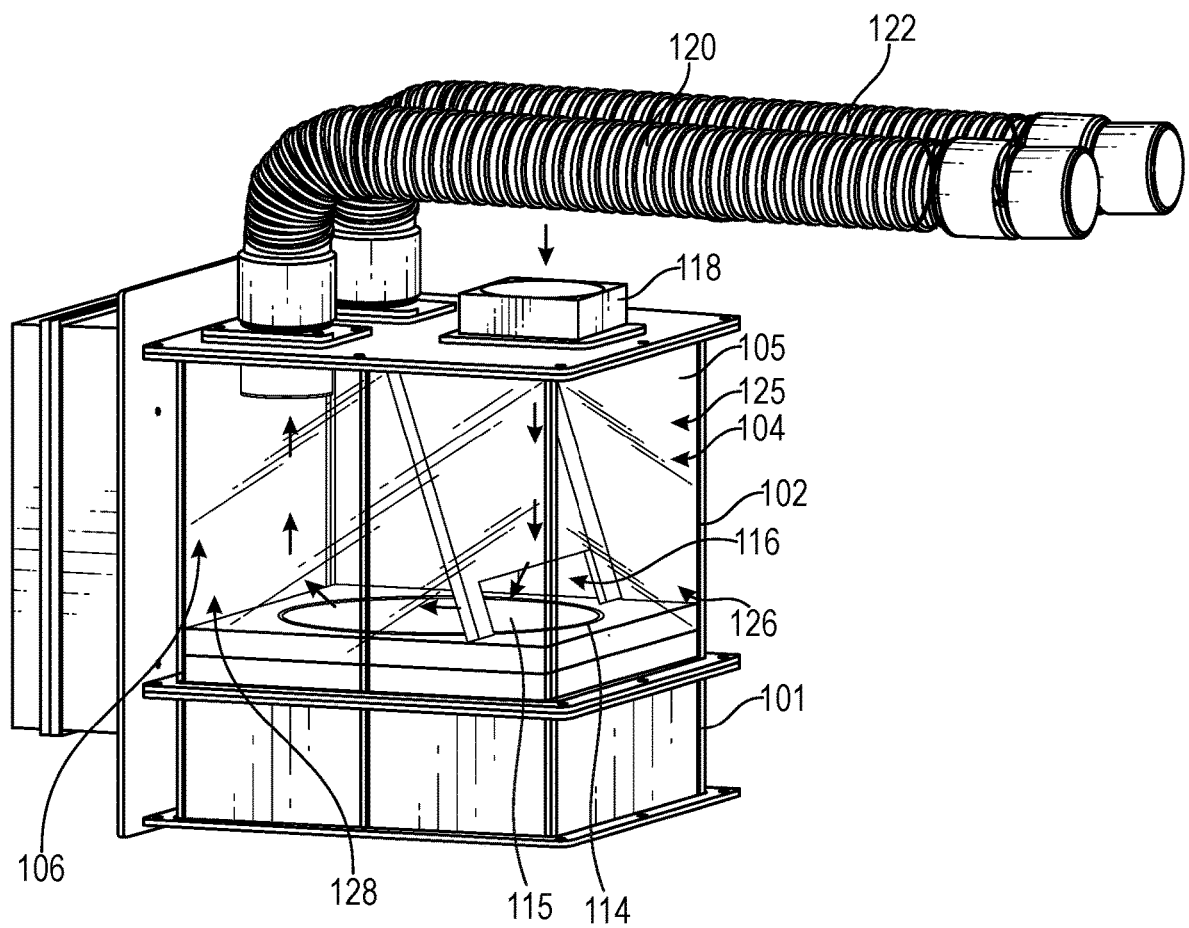
FIG. 8 illustrates a front, right side perspective view with arrows illustrating airflow of a dry mist generating apparatus.
Figure 9:
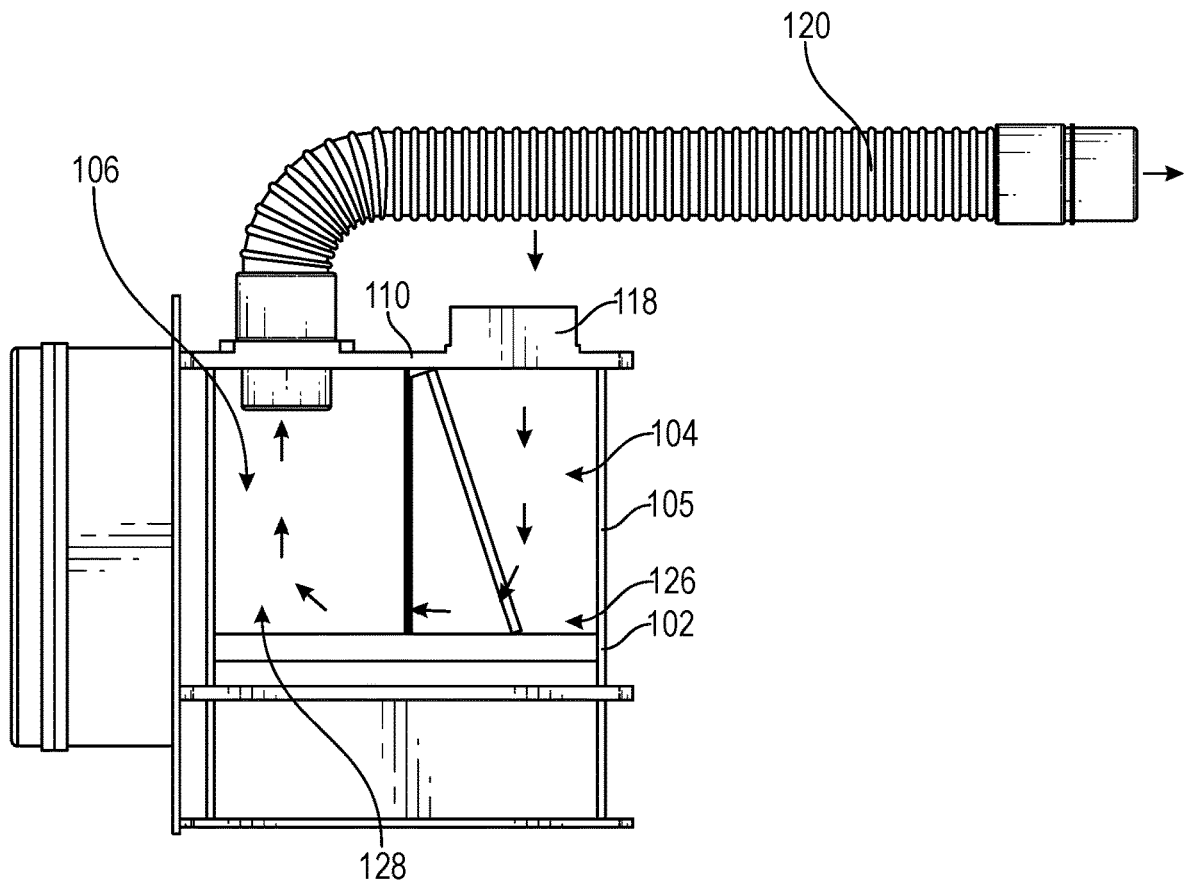
FIG. 9 illustrates a right elevation view with arrows illustrating airflow of a dry mist generating apparatus.
Figure 10:
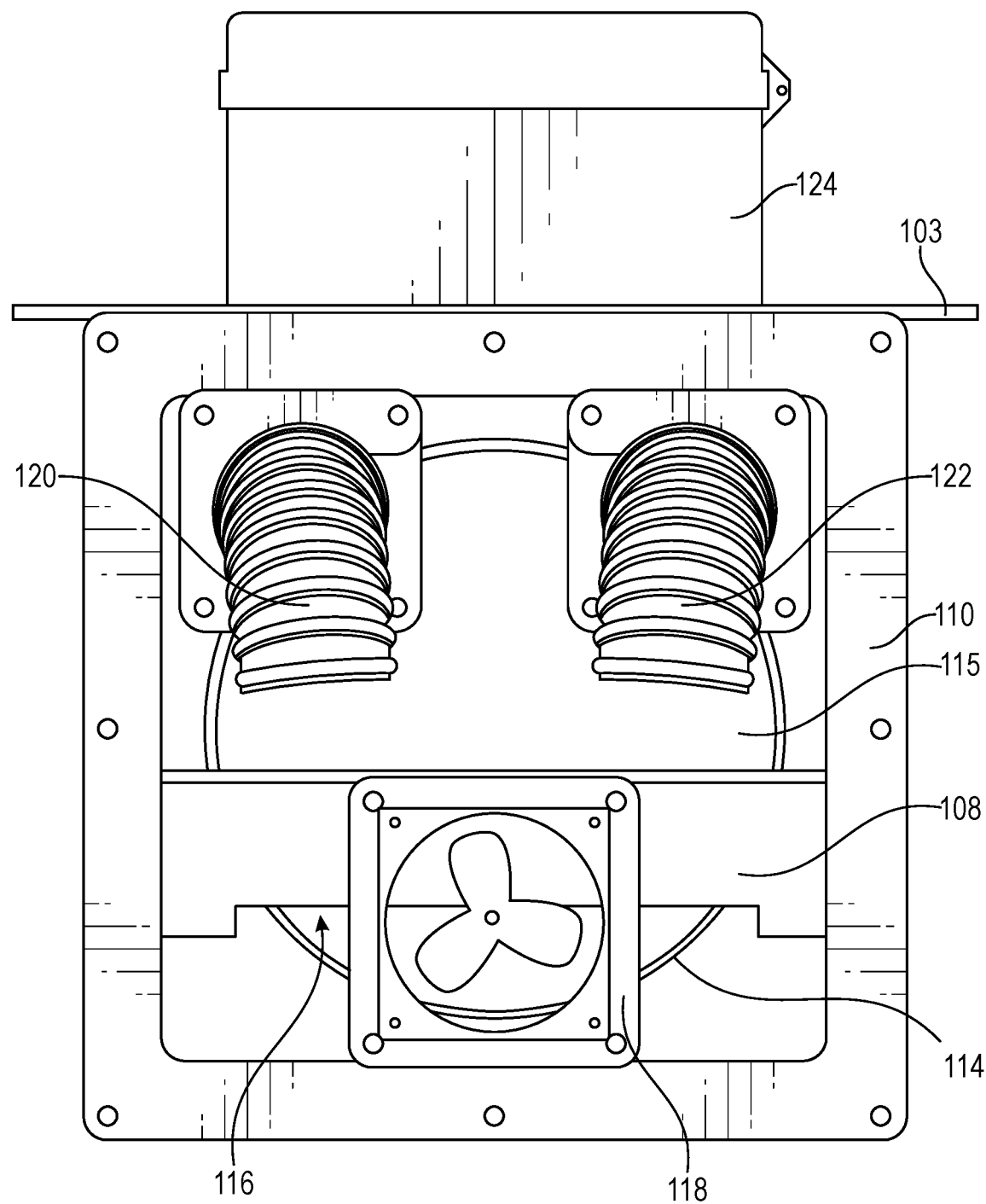
FIG. 10 illustrates a top plan view of a dry mist generating apparatus.
Figure 11:
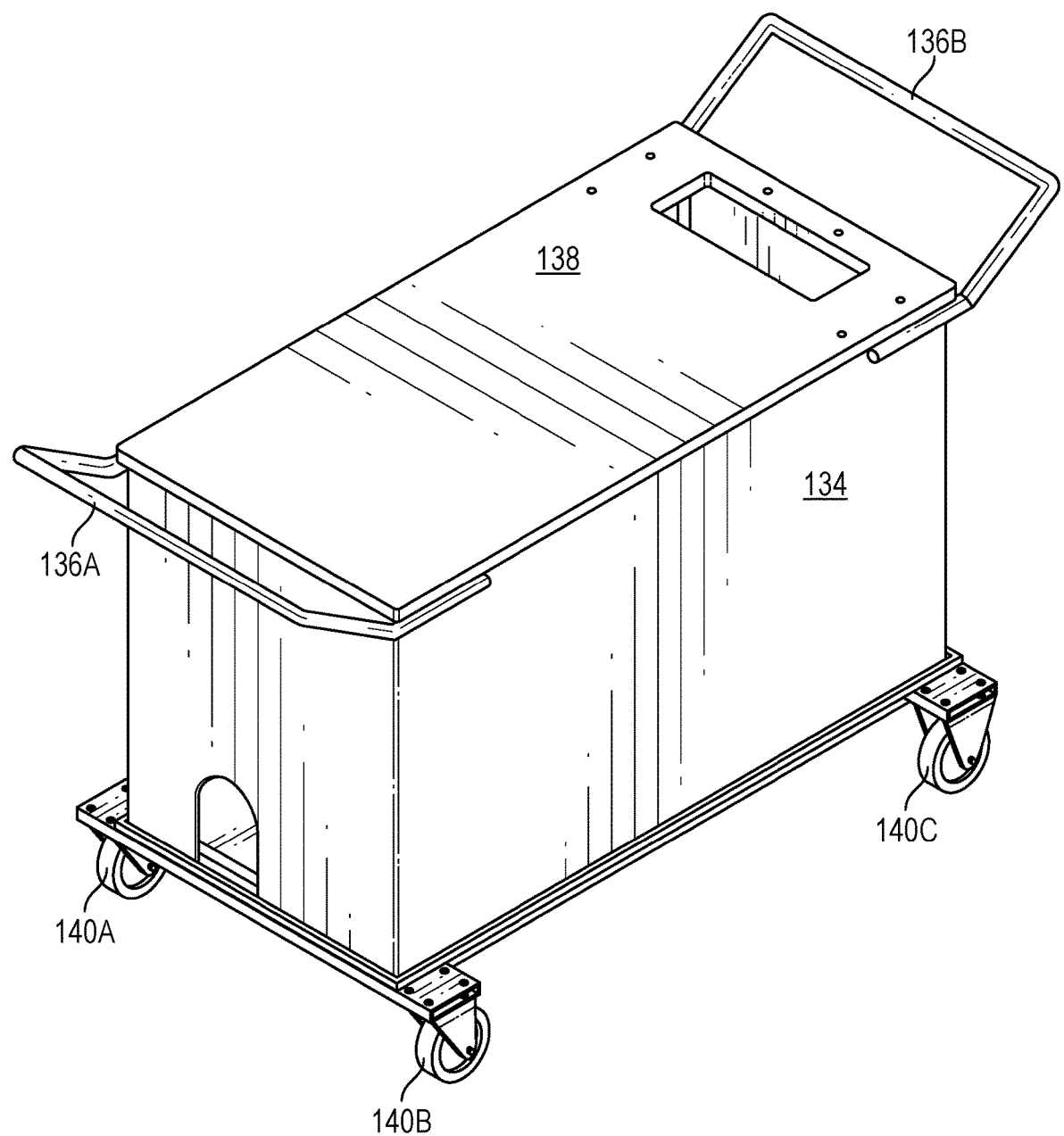
FIG. 11 illustrates a top, front, left side perspective view of a dry mist generating apparatus.

As shown in FIGS. 8-9, circular rotation air flow, which is turbulent and vortex, is induced into the first chamber 104 of the housing 102 using the fan 118. The air pathway is shown using arrows. Due to the angle of the diffuser plate 108, a narrow neck 126 is formed at the bottom of the first chamber 104. In other words, a top portion 125 of the first chamber 104 has a first distance from the diffuser plate 108 to a front wall 105 of the housing 102. The diffuser plate 108 is angled so that the lower end is closer to the front wall 105, forming the narrow neck 126. Because the turbulent and vortex air is compressed into the narrow neck 126 using the diffuser plate 108, the velocity of the air is increased, thereby increasing the pressure. The air then passes through the air aperture 116 of the diffuser plate 108 and above the ultrasonic transducer 115. As the air enters the second chamber 106, the larger volume space allows the air pressure to drop (e.g., Venturi effect) and the turbulent and vortex air flow from the first chamber 104 is flattened into straight laminar airflow over the ultrasonic transducer 115. The ultrasonic transducer 115 creates droplets, with some less than 10 microns in size. As the air passes into a bottom portion 128 of the second chamber 106, airflow is slowed, decreasing (e.g., Venturi effect). pressure and allowing accumulation. The heavier droplets fall while the smaller, sub-10 micron sized droplets proceed to the discharge tubes 120, 122. In some embodiments, it is preferable to produce droplets smaller than 5 microns so that they may pass through an HVAC unit, continuing to disinfect.

The length of the discharge tubes 120, 122, along with their diameter and bend, may be varied to achieve varying micron-sized droplets at discharge to the atmosphere. For example, the longer the discharge tubes 120, 122, the smaller the micron-sized droplets that exit. Conversely, shorter tubes 120, 122 allow for larger droplets to be expelled. Additionally, the size of the ultrasonic transducer may also be used to control the size of the droplets. Accordingly, a user may adjust the discharge tubes 120, 122 and their bends in order to achieve the maximum desired micron size of the droplets at an exit 130, 132 of each discharge tube 120, 122. In order to achieve micron sizes less than 4 microns, the discharge tubes 120, 122 are ideally non-linear, comprising bends as shown in FIGS. 12-13. By achieving droplets that have a size of less than 4 microns, the droplets remain suspended in the air and may freely flow therewith (defined herein as a "dry mist"). This dry mist is then able to penetrate all areas of a space or building as it flows through the air, thereby disinfecting the space or building as it penetrates.

In some embodiments, as shown in FIGS. 11-23, the dry mist generating apparatus 100 may be contained within a wheeled cart 134, the wheeled cart 134 comprising one or more handles 136A-B, a hinged lid 138, and a plurality of wheels 140A-D. As shown in FIGS. 12-13, the hinged lid 138 can secured in an open position, such as by using a rod 142, with the discharge tubes 120, 122 coupled to the hinged lid 138 such that they are raised with the hinged lid 138. As shown, the discharge tubes 120, 122 are non-linear (comprise bends), which thereby aids in collecting droplets greater than 4 microns in size. Referring to FIGS. 14-20, portions of the wheeled cart 134 have been removed for ease of viewing internal components. As understood, the wheeled cart 134 may comprise the dry mist generating apparatus 100, a first liquid holding tank 144, a second liquid holding tank 146, and a waste tank 148. As best seen in FIG. 15, the liquid holding tanks 144, 146 are elevated in relation to the housing 102. In other words, the bases of the liquid holding tanks 144, 146 are higher than the base 112 of the housing 102. As a result, liquid may be gravity-fed from the one or more liquid holding tanks 144, 146 to the housing 102 (which may be positioned on a riser 101 to achieve a desired height), such as through one or more pipes 150. One or more electric valves may be used to control the flow of liquid, as discussed later herein.

FIG. 16 illustrates a longitudinal cross-section of the wheeled cart 134 and the components therein. When closed, the exit 130, 132 of each discharge tube 120, 122 rests in a basin 152 that collects excess moisture, where it is directed to the waste tank 148 via a conduit 154. FIGS. 17-19 illustrate various angles of the wheeled cart 134 and its components.

FIG. 20 illustrates a top, detailed view of the wheeled cart 134 with the hinged lid 138 removed therefrom. The discharge tubes 120, 122 have also been removed from the ports 156, 158 in this view. Turning to FIGS. 21-22, liquid (e.g., Hypochlorous Acid (HOCL)) is able to flow from a first liquid holding tank 144 and liquid (e.g., water) is able to flow from a second holding tank 146 via at least one pipe 150. The HOCL may be controlled via an electric valve 160 and the water may be controlled via an electric valve 162. It will be appreciated that a coupler may be used to combine the liquid from both tanks 144, 146 once released from their respective electric valves 160, 162 and into a single pipe 150 for conveying to the housing 102. Further, the housing may comprise an outlet pipe 164 for releasing liquid from within the housing 102 when the dry mist generating apparatus 100 is not in operation. The outlet pipe 164 may be controlled via an electronic valve 166. The outlet pipe 164 exits at a position higher than where it enters the waste tank 148 so that it may be gravity fed as well.

In addition, the level of liquid within each tank 144, 146, and waste tank 148 may be monitored using sensors and the controller 124. For example, the HOCL tank may comprise a "full" liquid sensor 168 and a "low" liquid sensor 170. Likewise, the water tank may comprise a "full" liquid sensor 172 and a "low" liquid sensor 174. The waste tank 148 may comprise a "full" liquid sensor 176. Each liquid sensor is capable of detecting when liquid is in contact therewith, which is read by the controller 124, which is configured to control the on/off status of the apparatus as well as provide alerts to a user. For example, referring to FIG. 23, a user control panel 178 may comprise an on/off switch 180 and a plurality of indicators and/or switches 182A-I. The indicators/switches 182A-I may alert a user to high levels of liquid, low levels of liquid, a fault or error, or may reset the controller 124. The indicators may be lights (e.g., LEDs) or audible.

In one method of use, a user would maneuver the wheeled cart 134 to the desired location for disinfecting (or humidifying, or other use), would ensure that the first liquid holding tank 144 and second liquid holding tank 146 are full of the desired liquid. This may be determined by a user by reviewing the control panel 178 and the various indicators/switches 182A-I. The controller 124 is configured to control the indicators/switches 182A-I and may thereby indicate full or low status. With both tanks 144, 146 full, a user may open the hinged lid 138 and secure it in position. With the hinged lid 138 raised, the discharge tubes 120, 122 are angled upwardly (best seen in FIGS. 12-13).

A user may then start the dry mist generating apparatus 100 using the on/off switch 180. The controller 124 then actuates the electric valves 160, 162, allowing liquid from both tanks 144, 146 to be gravity fed to the housing 102. For sanitization, the liquid may be HOCL in the first tank 144 and water in the second tank 146. The ultrasonic transducer 115 converts the liquid into droplets sized 4 microns or less (the dry mist). As the transducer 115 creates the dry mist, the fan 118 induces air into the first chamber 104 where it passes to the second chamber 106 via the aperture 116, then upwardly to the discharge tubes 120, 122. As the air travels upward, the dry mist is likewise pulled with the air and up through the discharge tubes 120, 122. Due to the bends, angle, and length and diameter of the discharge tubes 120, 122, only dry mist (e.g., droplets of 4 microns or less) exit the discharge tubes at the exits 130, 132. Accordingly, it will be appreciated that a user may vary the angle, length, and diameter of the tubes to control the micron size of the droplets at the exits 130, 132.

The dry mist generating apparatus 100 will continue to operate until switched off by a user or until the controller 124 determines that a condition is met, such as that the run timer has reached the entered set point (10-240 minutes), or that the first tank 144 is low, the second tank 146 is low, or that the waste tank 148 is full, among other conditions. Because the HOCL exits as a dry mist, it is able to penetrate all areas of a room or building, thereby disinfecting both the air and surfaces. Because the HOCL is a dry mist, no residue remains and surfaces do not become wet—there is no need for any cleanup, which overcomes issues in the prior art.

It will be appreciated that the housing 102 may vary in size. In some embodiments, the housing 102 is sized so as to allow a user to easily carry the dry mist generating apparatus 100 for use and may comprises handles for easier carrying. In other embodiments, the housing 102 is too large to carry and must be pushed or otherwise transported using wheels either directly coupled to the housing 102 or on a cart as shown and described earlier.

As shown in FIG. 24, a dry mist generating apparatus 200 may comprise a plurality of discharge tubes 202A-D, a plurality of intake fans 204A-B, a plurality of ultrasonic transducers 206A-B, and a diffuser plate 208. Referring to FIG. 25, a dry mist generating apparatus 300 may comprise a plurality of discharge tubes 302A-D, a plurality of intake fans 304A-B, an ultrasonic transducer 306, and a diffuser plate 308. Accordingly, it is appreciated that the present invention is not limited to the number of fans, transducers, or discharge tubes.

Further, while liquid holding tanks 144, 146 were discussed above as feeding liquid to the housing 102, other configurations may be used without departing herefrom. For example, the housing 102 may comprise one or more threaded inlets (or other couplers) allowing for a bottle or other container to be threaded thereto. One or more bottles may then feed water and/or HOCL into the housing 102, either by manual flow valves or electronic flow valves. This allows the overall size to be reduced, allowing the system to carried by a user in some embodiments. For example, the housing 102 may comprise a handle allowing a user to carry it by hand. A user may then feed the desired liquid into the housing 102 via the coupled bottles where it can be turned into dry mist. The riser 101 may also function as a waste container in such a scenario. In the alternative, a waste container may be coupled to the housing 102. While embodiments discussed herein have generally discussed a portable dry mist generating apparatus, the present disclosure is not so limited. For example, the dry mist generating apparatus 100 may be coupled to an HVAC unit or may otherwise be secured to a building. Accordingly, it will be appreciated that the dry mist generating apparatus 100 may vary in size and may be portable or a fixture. Additionally, while plastic is used as an example herein, it will be appreciated that other corrosion resistant materials may be used, such as fiberglass, aluminum, carbon fiber, and others.

Because the droplets expelled from the discharge tubes 120, 122 have a micron size of 3 or less, the droplets are easily suspended in the air for extended times (i.e., a dry mist). This dry mist may be distributed in office spaces, schools, buildings, or any other enclosed area in need of disinfecting. Additionally, the dry mist may be distributed directly onto surfaces without creating wet surfaces. As a result, surface pathogens are neutralized. This is a significant improvement over the prior art, which does not remain airborne and causes wet surfaces.

Accordingly, the dry mist generating apparatus 100 solves the problems in the art, namely, the need for a disinfectant that can remain airborne for a significant amount of time, that may penetrate small spaces, that does not leave surfaces wet and that may produce this dry mist in an apparatus that is not susceptible to corrosion and other component failures.

It will be appreciated that systems and methods according to certain embodiments of the present disclosure may include, incorporate, or otherwise comprise properties or features (e.g., components, members, elements, parts, and/or portions) described in other embodiments. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment unless so stated. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

Exemplary embodiments are described above. No element, act, or instruction used in this description should be construed as important, necessary, critical, or essential unless explicitly described as such. Although only a few of the exemplary embodiments have been described in detail herein, those skilled in the art will readily appreciate that many modifications are possible in these exemplary embodiments without materially departing from the novel teachings and advantages herein. Accordingly, all such modifications are intended to be included within the scope of this invention.

What is claimed is:

1. A dry mist generating apparatus, comprising:

a wheeled cart;

a housing positioned within the wheeled cart, wherein a base of the housing is positioned at a first height;

a first liquid holding tank within the wheeled cart, wherein a base of the first liquid holding tank is positioned at a second height, which is higher than the first height, the first liquid holding tank comprising a first liquid sensor and a second liquid sensor;

a second liquid holding tank within the wheeled cart, wherein a base of the second liquid holding tank is positioned at the second height, which is higher than the first height, the second liquid holding tank comprising a first liquid sensor and a second liquid sensor;

at least one pipe for coupling the first liquid holding tank and the second liquid holding tank to the housing;

at least one electronic valve coupled to the at least one pipe for controlling a flow of liquid from the first and second liquid holding tanks to the housing;

a waste tank positioned beneath the first and second liquid holding tanks, the waste tank comprising a full liquid sensor;

wherein the housing comprises:

a diffuser plate positioned within the housing and extending from a top of the housing to a base of the housing, the diffuser plate positioned non-perpendicularly to the top of the housing and the base of the housing and separating the housing into a first chamber and a second chamber, a top portion of the first chamber comprising a first distance from the diffuser plate to a front wall and a lower portion of the first chamber comprising a second distance from the diffuser plate to the front wall, the second distance less than the first distance;

an ultrasonic transducer aperture in the base of the housing configured to receive an ultrasonic transducer, the diffuser plate comprising an air aperture straddling the ultrasonic transducer aperture;

a fan positioned on the top of the housing and configured to force air downward into the first chamber, wherein the air is compressed to a first pressure into the lower portion of the first chamber, the compressed air passing through the air aperture of the diffuser plate and over the ultrasonic transducer as it passes to a bottom portion of the second chamber, the air decompressing in the bottom portion to a second pressure less than the first pressure;

at least one discharge tube coupled to the top of the housing above the second chamber, wherein sub-10 micron-sized droplets in the second chamber flow upwardly to the at least one discharge tube, wherein the at least one discharge tube is coupled to a hinged lid on the wheeled cart, wherein when the hinged lid is in a closed position, the at least one discharge tube is enclosed within the wheeled cart with an exit of the least one discharge tube resting in a basin, wherein excess moisture in the basin is configured to flow to the waste tank via a conduit interposed between the first and second liquid holding tanks; and an outlet pipe coupled to the waste tank, the outlet pipe comprising an electronic valve;

a controller configured to control an on/off status of the ultrasonic transducer and the fan, and is further configured to control an open/closed status of the at least one electronic valve upon determining the status of:

a. the first and second liquid sensors of the first tank, b. the first and second liquid sensors of the second tank, and c. the full liquid sensor of the waste tank; and a user control panel comprising an on/off switch and a plurality of indicators.

* * * * *